US009028869B2

(12) United States Patent
Hite et al.

(10) Patent No.: US 9,028,869 B2
(45) Date of Patent: May 12, 2015

(54) MODIFIED RELEASE IBUPROFEN DOSAGE FORM

(75) Inventors: Michael Hite, Seattle, WA (US); Cathy Federici, Seattle, WA (US); Alan Brunelle, Woodinville, WA (US); Stephen Turner, Snoqualmie, WA (US)

(73) Assignee: Shasun Pharmaceuticals Limited, Chennai, Tamil Nadu (IN)

( * ) Notice: Subject to any disclaimer, the term of this patent is extended or adjusted under 35 U.S.C. 154(b) by 569 days.

(21) Appl. No.: 12/706,429

(22) Filed: Feb. 16, 2010

(65) Prior Publication Data
US 2010/0143466 A1 Jun. 10, 2010

Related U.S. Application Data

(63) Continuation of application No. 11/633,322, filed on Dec. 4, 2006, now abandoned, which is a continuation-in-part of application No. 11/238,802, filed on Sep. 29, 2005, now abandoned.

(60) Provisional application No. 60/689,631, filed on Jun. 10, 2005, provisional application No. 60/614,932, filed on Sep. 30, 2004.

(51) Int. Cl.
*A61K 9/20* (2006.01)
*A61K 31/19* (2006.01)
*A61K 31/192* (2006.01)
*A61K 47/02* (2006.01)
*A61K 47/18* (2006.01)
*A61K 47/38* (2006.01)

(52) U.S. Cl.
CPC ............ *A61K 9/2013* (2013.01); *A61K 9/2009* (2013.01); *A61K 9/2031* (2013.01); *A61K 9/2054* (2013.01); *A61K 31/192* (2013.01); *A61K 47/02* (2013.01); *A61K 47/183* (2013.01); *A61K 47/38* (2013.01)

(58) Field of Classification Search
CPC .... A61K 9/2054; A61K 47/38; A61K 31/192
See application file for complete search history.

(56) References Cited

U.S. PATENT DOCUMENTS

| 4,097,606 A * | 6/1978 | Chavkin et al. ............... 514/629 |
| 4,389,393 A | 6/1983 | Schor et al. |
| 4,609,675 A | 9/1986 | Franz |
| 4,814,181 A | 3/1989 | Jordan et al. |
| 4,871,548 A | 10/1989 | Edgren et al. |
| 4,877,620 A | 10/1989 | Loew et al. |
| 4,888,343 A * | 12/1989 | Jones et al. ............... 514/263.31 |
| 4,916,161 A | 4/1990 | Patell |
| 4,937,080 A | 6/1990 | Appelgren et al. |
| 4,990,535 A | 2/1991 | Cho et al. |
| 5,009,895 A * | 4/1991 | Lui ............................. 424/465 |
| 5,087,454 A | 2/1992 | Duerholz et al. |
| 5,100,675 A | 3/1992 | Cho et al. |
| 5,104,648 A | 4/1992 | Denton et al. |
| 5,415,871 A | 5/1995 | Pankhania et al. |
| 5,429,825 A | 7/1995 | Reo et al. |
| 5,462,747 A | 10/1995 | Radebaugh et al. |
| 5,482,718 A * | 1/1996 | Shah et al. .................... 424/480 |
| 5,512,300 A | 4/1996 | Weng et al. |
| 5,739,165 A | 4/1998 | Makino et al. |
| 5,830,503 A | 11/1998 | Chen |
| 5,997,905 A | 12/1999 | McTeigue et al. |
| 6,008,249 A * | 12/1999 | Gajdos et al. ................ 514/561 |
| 6,197,336 B1 | 3/2001 | Grassano |
| 6,358,525 B1 | 3/2002 | Guo et al. |
| 6,361,794 B1 | 3/2002 | Kushla et al. |
| 6,548,083 B1 | 4/2003 | Wong et al. |
| 6,592,901 B2 | 7/2003 | Durig et al. |
| 6,599,531 B2 | 7/2003 | Kushla et al. |
| 6,623,756 B1 | 9/2003 | Wilber et al. |
| 6,936,632 B2 | 8/2005 | Striegel et al. |
| 2002/0034540 A1 | 3/2002 | Price |
| 2003/0026834 A1* | 2/2003 | Jamali .......................... 424/465 |
| 2003/0045580 A1 | 3/2003 | Einig |
| 2003/0068368 A1 | 4/2003 | Kushla et al. |
| 2003/0153623 A1 | 8/2003 | Kishimoto et al. |
| 2003/0175341 A1 | 9/2003 | Rampal et al. |
| 2004/0047904 A1 | 3/2004 | Ohta et al. |
| 2004/0048924 A1 | 3/2004 | Bunick et al. |

(Continued)

FOREIGN PATENT DOCUMENTS

| CN | 1215989 | 5/1999 |
| CN | 1246795 | 3/2000 |

(Continued)

OTHER PUBLICATIONS

Edge et al. (In Polysaccharide Applications; El-Nokaly, M., et al; ACS Symposium Series; American Chemical Society; Washington, DC, 98-112, 1999) Polysaccharide Engineering: Silicified Micrtocrystalline cellulose . . .*

FMC Problem Solver and Reference Manual (2001 FMC Corporation, Philadelphia, PA), 1998.

USPTO Office Action for U.S. Appl. No. 11/238,802 mailed on Sep. 30, 2009.

International Search Report corresponding to application No. PCT/US2007/024496 dated Jul. 18, 2008.

(Continued)

*Primary Examiner* — David Blanchard
*Assistant Examiner* — Tigabu Kassa
(74) *Attorney, Agent, or Firm* — Taft Stettinius & Hollister LLP

(57) ABSTRACT

The present invention is a solid dosage form for oral administration of ibuprofen comprising a modified release formulation of ibuprofen which provides an immediate burst effect and thereafter a sustained release of sufficient ibuprofen to maintain blood levels at least 6.4 µg/ml over an extended period of at least 8 hours following administering of a single dose.

15 Claims, 19 Drawing Sheets

(56) References Cited

U.S. PATENT DOCUMENTS

| | | | |
|---|---|---|---|
| 2004/0081701 A1 | 4/2004 | Erkoboni et al. |
| 2004/0096497 A1 | 5/2004 | Ponder et al. |
| 2004/0102522 A1 | 5/2004 | Gruber et al. |
| 2004/0121012 A1 | 6/2004 | Baichwal |
| 2004/0186122 A1 | 9/2004 | Newman et al. |
| 2004/0204403 A1 | 10/2004 | Pankhania et al. |
| 2004/0219220 A1 | 11/2004 | Sherry et al. |
| 2004/0265378 A1 | 12/2004 | Peng et al. |
| 2007/0077297 A1 | 4/2007 | Hite et al. |

FOREIGN PATENT DOCUMENTS

| | | |
|---|---|---|
| DE | 100 03 757 | 8/2001 |
| EP | 0297866 | 1/1989 |
| EP | 1444978 | 8/2004 |
| JP | 7-53364 | 2/1995 |
| JP | 2000-507922 | 6/2000 |
| JP | 2003-525223 | 8/2003 |
| JP | 2004175690 * | 6/2004 |
| JP | 2006-248922 | 9/2006 |
| JP | 2009-511537 | 3/2007 |
| WO | WO 88/08299 | 11/1988 |
| WO | WO 97/30699 | 8/1997 |
| WO | WO 98/34612 | 8/1998 |
| WO | WO 00/07570 | 2/2000 |
| WO | WO 00/54752 | 9/2000 |
| WO | WO 03/063825 | 8/2003 |
| WO | WO 2004/032909 A2 | 4/2004 |
| WO | WO 2004/037190 A2 | 5/2004 |
| WO | WO 2006/039692 | 4/2006 |

OTHER PUBLICATIONS

International Search Report corresponding to application No. PCT/US2007/024489 dated Aug. 12, 2008.
International Search Report corresponding to application No. PCT/US2005/35630 dated Apr. 19, 2006.
Supplementary European Search Report corresponding to EP Application No. 05805851.2 dated Apr. 1, 2010.

* cited by examiner

MODIFIED RELEASE IBUPROFEN DOSAGE FORM

CROSS REFERENCE TO RELATED APPLICATIONS

The present invention is a continuation of U.S. patent application Ser. No. 11/633,322, filed Dec. 4, 2006, now abandoned, which is a continuation-in-part of U.S. application Ser. No. 11/238,802, filed Sep. 29, 2005, now abandoned, which claims the benefit of U.S. Provisional Applications Nos. 60/614,932, filed Sep. 30, 2004 and 60/689,631, filed Jun. 10, 2005, the disclosures of all of which are incorporated herein by reference in their entirety.

BACKGROUND OF THE INVENTION

Ibuprofen is 2-(4-isobutylphenyl)propionic acid and is a non-steroidal anti-inflammatory compound (NSAID), which exhibits high levels of anti-inflammatory, analgesic and anti-pyretic activities necessary for the effective treatment of rheumatoid arthritis and osteo-arthritis and other inflammatory conditions. Most dosage forms of ibuprofen are immediate release dosage forms that provide rapid onset of therapeutic action, then rapidly declining levels of active ingredient, necessitating repeated dosing. They do not maintain therapeutic levels from one treatment over an extended period of time. Repeat dosing is thus required at intervals of four to six hours. Formulations that claim extended release fail to have an initial burst of the drug and thus exhibit substantial delay between administration and the achievement of an effective therapeutic blood level. Therefore, a need exists for a solid dosage form, for example a compressed tablet, which provides an initial burst of released ibuprofen, leading to prompt onset of action, then thereafter provides a sustained release of sufficient ibuprofen to maintain beneficial blood levels of ibuprofen over an extended period of 8 or more hours.

It is known ibuprofen is not directly compressible, and attempts to directly manufacture ibuprofen results in tablets which stick to the faces of the tableting press, are too friable for storage or transport, or split into two or more segments when expelled from the tableting press. To circumvent those manufacturing problems, those skilled in the art carry out a preliminary step prior to tableting, in which ibuprofen is wet granulated with a microcrystalline cellulose additive to form a granular composition comprising ibuprofen and microcrystalline cellulose, which is then capable of blending with further excipients and/or is directly compressible for the manufacture of a suitable solid dosage form. Therefore, a need exists for a dry blend of ibuprofen which is suitable for manufacture of a satisfactory tableted dosage form, obviating the need for a pre-granulation step.

SUMMARY OF THE INVENTION

In accordance with the foregoing, we have provided a solid dosage form for oral administration of ibuprofen comprising a modified release formulation of ibuprofen which provides an immediate burst effect and thereafter a sustained release of sufficient ibuprofen to maintain blood levels at least 6.4 µg/ml over an extended period of at least 8 hours following administration of a single dose.

More particularly, the invention comprises a solid dosage form for oral administration comprising a hydrophilic polymer, a pharmaceutically effective amount of ibuprofen in the range of 300 mg to 800 mg uniformly dispersed in the polymer, a dissolution additive dispersed in the polymer in an amount in the range of 10% to 35% by weight of the ibuprofen, and a formulation additive dispersed in the polymer in an amount of 15% to 75% by weight of the ibuprofen. The dosage form releases ibuprofen at a rate sufficient to initially deliver an effective amount of ibuprofen within about 2.0 hours following administration. The dosage form then subsequently delivers the remaining amount of ibuprofen at a relatively constant rate sufficient to maintain a level of ibuprofen over a predetermined delivery period of for at least 8 hours.

As used herein, a relative constant rate refers to a substantially linear relationship shown in the examples following the initial burst (up to about 2 hours) between percentage released and elapsed time.

DETAILED DESCRIPTION OF THE INVENTION

Figure 1:
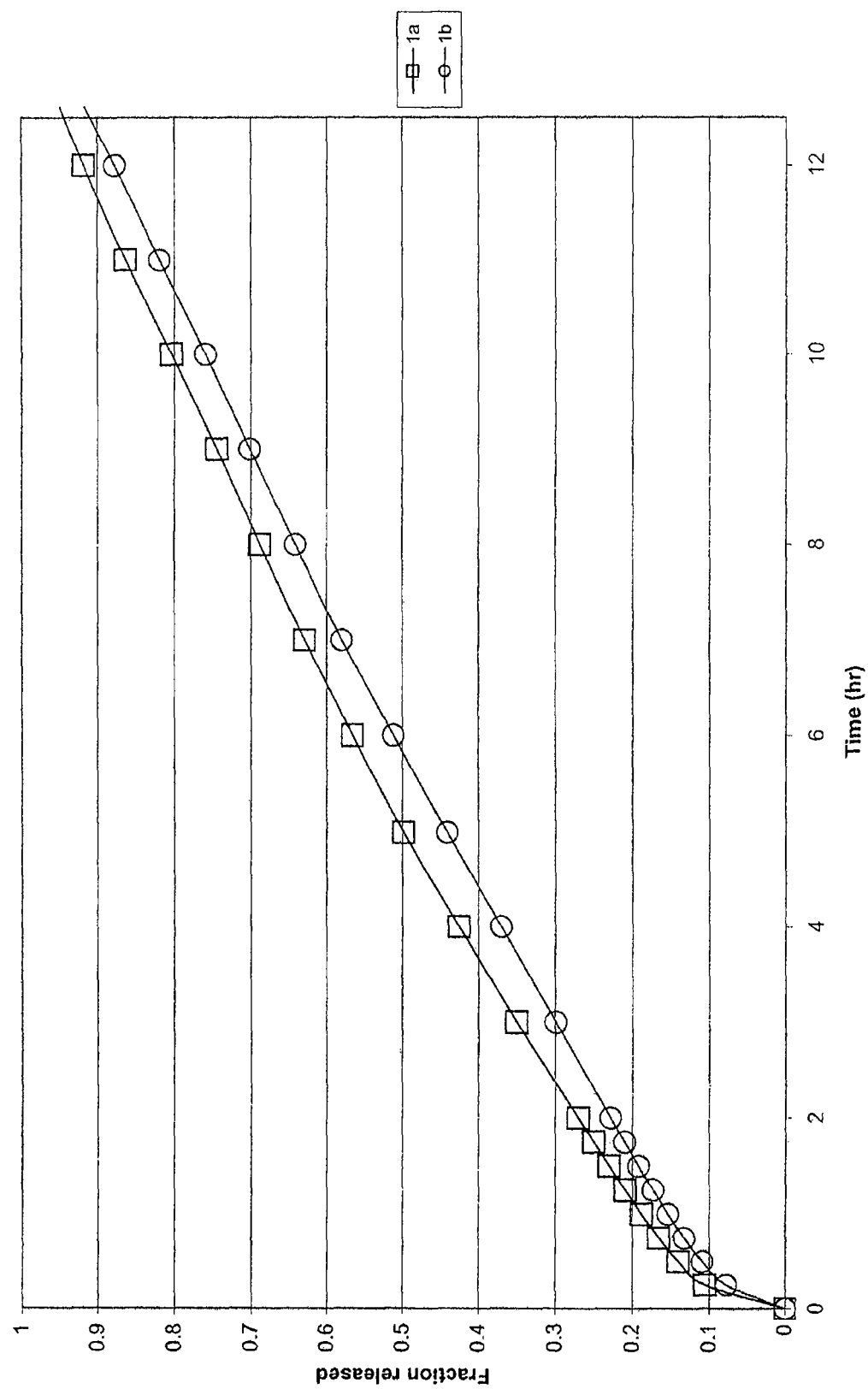
FIG. 1: In-vitro dissolution of Example 1

The present invention is further illustrated and described by reference to the following disclosure, examples and discussion below. In the examples and discussion which follow, the use of particular polymers, electrolytes, additives, fillers and tableting aids are provided by way of example only and are not intended to limit the scope of this invention. Although the invention is illustrated and described herein with reference to specific embodiments, the invention is not intended to be limited to the details shown. Rather, various modifications may be made in the details within the scope and range of equivalents of the claims and without departing from the invention.

The ibuprofen content of the dosage form may be between in the range about 300 mg and about 800 mg per dosage unit, for example about 300, 400 or 600 mg per unit dosage form. Also contemplated is using prodrugs of ibuprofen such as ibuprofen-lysine and ibuprofen-arginine. If a smaller dosage form is desired, a single dose of ibuprofen may be divided between multiple, for example two to three, dosage units, such as tablets, which may be administered at substantially the same time. The dosage form may comprise from about 25% to about 75% by weight ibuprofen.

The hydrophilic polymer used in the dosage form may be selected from a wide variety of hydrophilic polymers. Hydrophilic polymers suitable for use in the sustained release formulation include: one or more natural or partially or totally synthetic hydrophilic gums such as acacia, gum tragacanth, locust bean gum, guar gum, or karaya gum; modified cellulosic substances such as methylcellulose, hydroxy methylcellulose, hydroxypropyl methylcellulose, hydroxypropyl cellulose, hydroxyethylcellulose, or carboxyethylcellulose; proteinaceous substances such as agar, pectin, carrageenan, gelatin, casein, zein and alginates; and other hydrophilic polymers such as carboxypolymethylene, bentonite, magnesium aluminum silicate, polysaccharides, modified starch derivatives, and other hydrophilic polymers known to those of skill in the art, or a combination of such polymers.

These hydrophilic polymers gel and dissolve slowly in aqueous acidic media thereby allowing the ibuprofen to diffuse from the gel in the stomach and gastrointestinal tract. Hydroxypropyl methylcellulose (HPMC) and other hydrophilic polymers mentioned above may be available in forms that have varying viscosity ratings. In general these polymers, or the combination of them, may be present in the dosage form alone or in combination in an amount or at a concentration in the range of about 10% to about 70% by weight of the ibuprofen present in the formulation, for example about 10% to about 50% or about 10% to about 35%, depending on the release pattern which is sought to be achieved with the particular dosage form.

One hydrophilic polymer useful in the present invention is HPMC K4M. This is a nonionic swellable hydrophilic polymer manufactured by The Dow Chemical Company under the tradename "Methocel." HPMC K4M is also referred to as HPMC K4MP, in which the "P" refers to premium cellulose ether designed for pharmaceutical formulations. The "4" in the abbreviation suggests that the polymer has a nominal viscosity (2% in water) of 4000. The percent of methoxyl and hydroxypropyl groups are 19-24 and 7-12, respectively. In its physical form, HPMC K4M is a free-flowing, off-white powder with a particle size limitation of 90%<100 mesh screen. A more complete list of HPMC includes K100LVP, K15MP, K100MP, E4MP and E10MP CR with nominal viscosities of 100, 15000, 100000, 4000, and 10000 respectively.

In one embodiment a formulation is provided in which the hydrophilic polymer comprises two viscosities of HPMC employed at the same or different percentages relative to the amount of ibuprofen present in the formulation. For example, a low viscosity HPMC such as HPMC 100LV may be used at a concentration in the range of about 10% to about 20% in combination with a higher viscosity HPMC, for example HPMC, such as HPMC K4M, HPMC K15M or HPMC K100M, at a concentration which may be substantially the same or a different viscosity in the range of about 10-30%, in which the combined amounts of HPMC employed in the formulation is in the range of about 30% to about 40% relative to the amount of ibuprofen present in the formulation. In one example there is employed about 11% HPMC K100LV in combination with about 21% of HPMC K4M, a total of about 32% HPMC based on the amount of ibuprofen present in the formulation, in which the weight ratio of the higher viscosity to the lower viscosity HPMC is about 2:1.

The solid dosage form also includes at least one formulation additive such as one or more of a filler, a diluent or a compression aid. These are additives well known to those skilled in the art which aid in preparation or manufacture of the dosage form. For a tableted solid dosage form a tableting aid such as microcrystalline cellulose (MCC), such as MCC 105 (particle size of about 20 μm), MCC 200 (particle size of about 180 μm) and MCC 302 (particle size of about 90 μm), which as used herein includes silicified microcrystalline cellulose (MCC bonded to SiO$_2$), such as Prosolv 90 (particle size of about 110 μm) and Prosolv 50 (particle size of about 60 μm); lactose, such as spray dried lactose (Lactopress®); dicalcium phosphate; silica; pregelatinized starch; and combinations thereof may be incorporated into the formulation in an amount or at a concentration in the range of about 15% to about 75% by weight of the ibuprofen present in the dosage form. It is contemplated that various particle sizes of microcrystalline cellulose may be used if desired, for example two different particle sizes in which each of them are present in individual amounts in the range of 17% to 35% by weight of the ibuprofen present in the formulation.

In one embodiment a formulation is provided in which the formulation additive comprises silicified microcrystalline cellulose present at two different particle sizes ranging from 60 μm to 110 μm. For example, a formulation additive may comprise two different particle sizes of Prosolv™ microcrystalline cellulose, wherein for example Prosolv50 (particle size 60 μm) is present in combination with a Prosolv90 (particle size 110 μm), suitably at a weight ratio in the range of about 1:1 to about 2:1, with the combination being present at a concentration of about 40% to about 60% by weight of the ibuprofen present in the formulation. This embodiment may suitably be used in combination with a hydrophilic polymer having two different particle sizes as exemplified and described above, for example HPMC K100LV and HPMC K4M.

In addition to formulation additives, the dosage form also contains at least one dissolution additive. Such additives which generally comprise a pore-forming, wetting or disintegration agent which facilitates dissolution of the dosage form. Such dissolution additives may be present in the dosage form at an amount or concentration in the range of about 10% to about 35% by weight of the ibuprofen, for example, at 10-20%. The additive may suitably be selected from alkali metal salts, such as sodium and potassium carbonate; sodium carbonate, monohydrate; sodium bicarbonate; amino acids with neutral-to-basic side chains, such as glycine, alanine, valine, leucine, iso-leucine, cysteine, methionine, phenylalanine, proline, lysine, arginine, histidine, serine, threonine, asparagine, tryptophan, tyrosine and glutamine; conventional pharmaceutical disintegrants and combinations or mixtures thereof. Examples of such additives are sodium carbonate, glycine, arginine and croscarmellose sodium.

In one embodiment, a formulation is provided in which the dissolution additive comprises two different additives wherein the dissolution additive is present in a combined range of about 10-20% by weight of ibuprofen. For example, a croscarmellose sodium may be present in combination with a second dissolution additive glycine wherein the combined range of the croscarmellose sodium and gycline is about 10-20% by weight of ibuprofen.

In accordance with a process aspect of this invention, manufacture of ibuprofen tablets improved by pre-blending ibuprofen with silica or a combination of silica and microcrystalline cellulose. form. The process of pre-blending ibuprofen with silica, or a combination of silica and microcrystalline cellulose improves manufacturability of the dosage form and reduces the tendency of the dosage form to fracture, or stick to the faces of the compression machine. The pre-blending duration can range from about 15 minutes to about 60 minutes with significant improvement as blending time is increased to at least 30-40 minutes. Blending can be performed in several different sizes of V-blenders and at several different speeds. In one embodiment, blending can be performed in a 16 qt V-blender (<1 ft$^3$) at 36 rpm while in another embodiment blending can be performed in a 40 ft$^3$ V-blender at 10 rpm. The resulting dry pre-blend, suitably in the form of a finely divided powder, may then blended with the remaining excipients and the resulting composition directly compressed into a satisfactory tableted dosage form.

In addition to ibuprofen, multiple active ingredients are contemplated and may be present in the present dosage form. Combinations of ibuprofen with actives such as caffeine, aspirin, pseudoephedrine, phenylephrine and/or other sympathomimetics, analgesics, such as hydrocodone, and antihistamines are within the scope of the invention.

Favorable in vitro characteristics that lead to an acceptable in vivo efficacy are contemplated as 20% or greater release within 2.0 hours after oral administration or contact with an aqueous environment, followed by more gradual release over several hours, leading to release of at least 70% release in 8 to 12 hours following administration or contact with an aqueous environment. The method of determining in vitro release is using an agitated aqueous medium, such as stirring at 50 rpm in pH 7.2 $KH_2PO_4$ media; or surrogate methods using alternate pH media, such as 0.1N HCl or SGF @ pH 1.2 for an initial (30 min-2 hr period or using alternate hydrodynamic conditions such as 100 to 150 rpm for a period of 1-2 hrs).

The accepted range for minimal efficacy in vivo is from about 6.4 µg/ml to about 10 µg/ml mean ibuprofen blood concentration. The present invention is capable of quickly achieving these levels within 2 hours of oral administration, and maintaining such levels for a period of 8 to 12 hours depending on the amount of ibuprofen administered and the dosing regimen.

EXAMPLES

The formulations of the invention are illustrated by the following examples. The use of particular polymers, electrolytes, additives, fillers and compression aids are not intended to limit the scope of this invention but are exemplary only.

Figure 19:
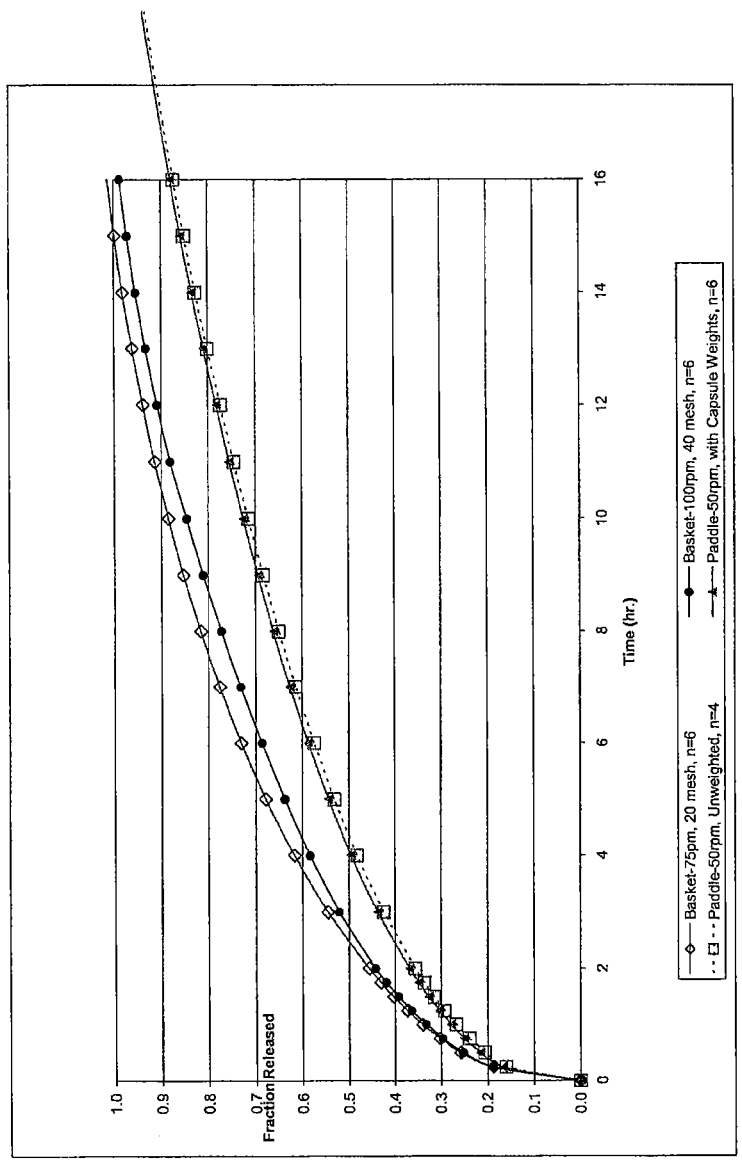
FIG. 19: In-vitro dissolution of Example 21

The solid dosage comprising a modified release formulation of the present invention was prepared and tested for both in vitro release and in vivo blood levels as described in Examples 1-20 below. In the in vivo testing, the dissolution rates of the subject dosage forms were compared against two commercially available tablets, one being an immediate release formulation of 200 mg of ibuprofen and the other being an immediate release 600 mg ibuprofen formulation. The solid dosage forms comprising the modified release formulation of the present invention demonstrated an initial burst similar to an immediate release tablet and a slower, more controlled release of ibuprofen over a eight hour period, as best seen in FIG. 19.

Unless otherwise noted, all in vitro release performance was evaluated in a type II dissolution apparatus in 900 mL $KH_2PO_4$ buffer, pH 7.2, at 50 rpm paddle speed.

Example 1

In one embodiment, the formulation comprised ibuprofen, hydroxypropyl methylcellulose (HPMC K15M and HPMC K100LV), glycine and sodium carbonate, in which HPMC K15M was present at a concentration of 18% by weight of ibuprofen, Ex. 1a, and at a concentration of 21% by weight of ibuprofen, Ex. 1b, HPMC K100LV was present at a concentration of 17% by weight of ibuprofen, glycine was present at a concentration of 2.5% by weight of ibuprofen, and sodium carbonate was present at a concentration of 17% by weight of ibuprofen within a monolithic compressed tablet. The specific formulations are as follows:

| Ex. 1a | mg |
|---|---|
| Ibuprofen 90 grade | 600 |
| HPMC K15M | 110 |
| HPMC K100LV | 100 |
| MCC PH102 | 100 |
| $Na_2CO_3$, anhydrous | 150 |
| Glycine | 15 |
| Silica, Syloid 244 | 20 |
| Mg Stearate | 10 |
| Total: | 1105 |

| Ex. 1b | mg |
|---|---|
| Ibuprofen 90 grade | 600 |
| HPMC K15M | 125 |
| HPMC K100LV | 100 |
| MCC PH102 | 100 |
| $Na_2CO_3$, anhydrous | 150 |
| Glycine | 15 |
| Silica, Syloid 244 | 20 |
| Mg Stearate | 10 |
| Total: | 1120 |

All ingredients were passed through a 30-mesh screen and blended with the remaining formulation components in a V-blender. The resulting powder was compressed into tablets using conventional compression techniques.

As shown in FIG. 1, the results of this Example demonstrate that the invention is capable of an in vitro release profile comprising a burst effect, followed by the sustained release of the remaining material, leading to in excess of 90% release in approximately 12 hours. This formulation thus overcomes one of the principle problems with many ibuprofen formulations which exhibit substantially less than complete release over an extended period of time.

Example 2

In another embodiment, the formulation comprised ibuprofen, hydroxypropyl methylcellulose (HPMC K100M and HPMC K100LV), sodium carbonate, flow agents and tableting aids, in which HPMC K100M was present at a concentration of 17% by weight of ibuprofen, HPMC K100LV was present at a concentration of 17% by weight of ibuprofen, and sodium carbonate was present at a concentration of 25% by weight of ibuprofen within a compressed monolithic tablet. The specific formula is as follows:

| Ex. 2 | mg |
|---|---|
| Ibuprofen | 600 |
| HPMC K100M | 100 |
| HPMC K100LV | 100 |
| $Na_2CO_3$, anhydrous | 150 |
| MCC PH102 | 150 |
| Silica, Syloid 244 | 20 |
| Mg Stearate | 10 |
| Total: | 1130 |

The formulation components were mixed in a V-blender. The resulting powder was compressed into tablets using conventional technologies. In this Example a combination of a medium to high viscosity HPMC and a low viscosity HPMC were used.

Figure 2:
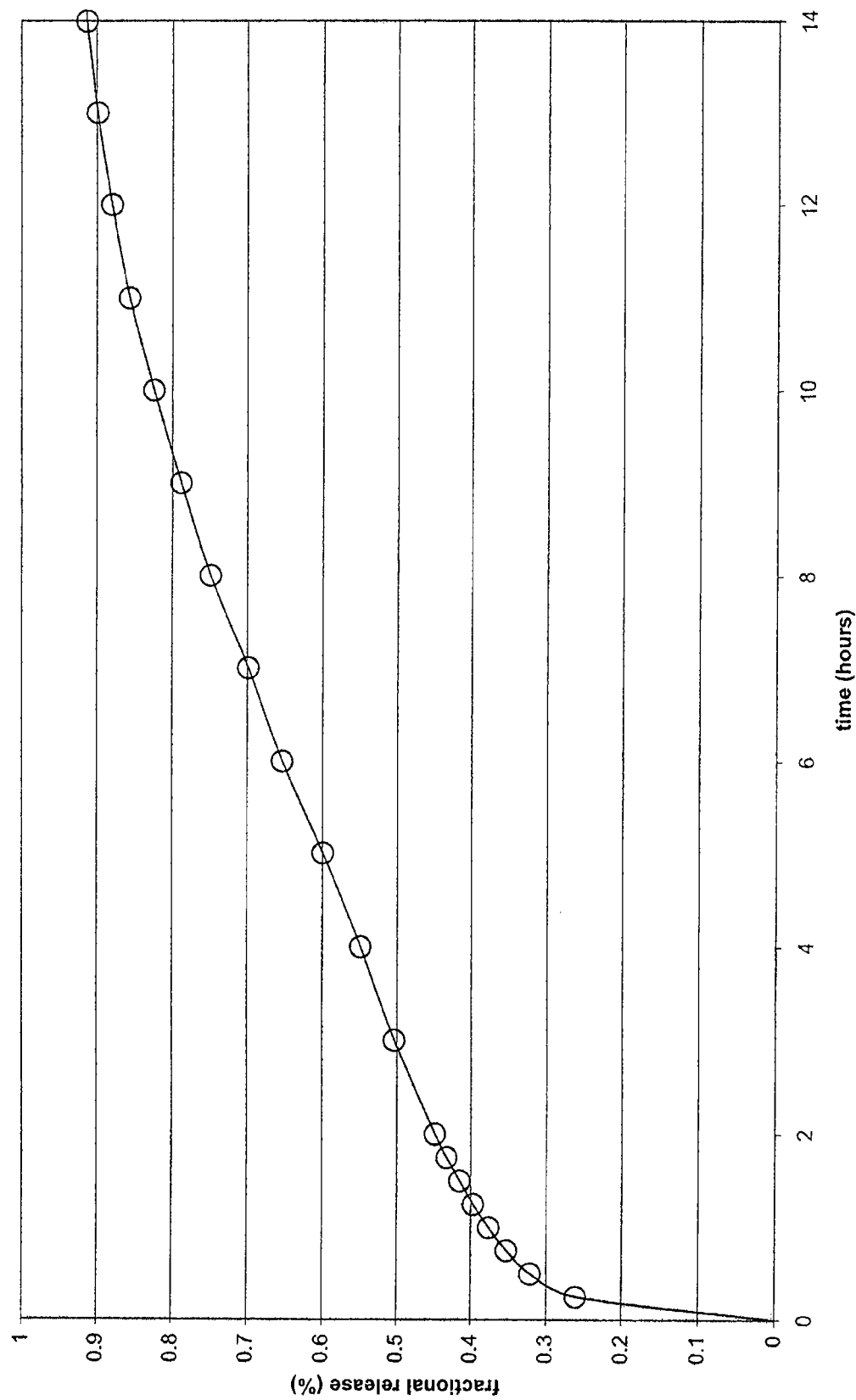
FIG. 2: In-vitro dissolution of Example 2

As shown in FIG. 2, the results of this Example demonstrate an in vitro release profile comprising a burst effect, followed by the sustained release of the remaining material. The burst effect provides release of 20% of ibuprofen within 2 hours, and the release of approximately 90% of the available ibuprofen over a period of 12 to 14 hours.

Example 3

In another embodiment, the formulation comprised ibuprofen, hydroxypropyl methylcellulose (HPMC K15M and HPMC K100LV), sodium carbonate, glycine, flow agents and tableting aids, in which HPMC K15M was present at a concentration of 17% by weight of ibuprofen, HPMC K100LV was present at a concentration of 17% by weight of ibuprofen and sodium carbonate was present at a concentration of 25% by weight of ibuprofen within a compressed monolithic tablet.

| Ex. 3 | mg |
| --- | --- |
| Ibuprofen | 600 |
| HPMC K15M | 100 |
| HPMC K100LV | 100 |
| MCC PH102 | 100 |
| $Na_2CO_3$, anhydrous | 150 |
| Glycine | 15 |
| Silica, Syloid 244 | 20 |
| Mg Stearate | 10 |
| Total: | 1095 |

The formulation components were mixed in a V-blender. The resulting powder was compressed into tablets using conventional compression technology. In this Example a combination of a medium to high viscosity HPMC and a low viscosity HPMC was used.

Figure 3:
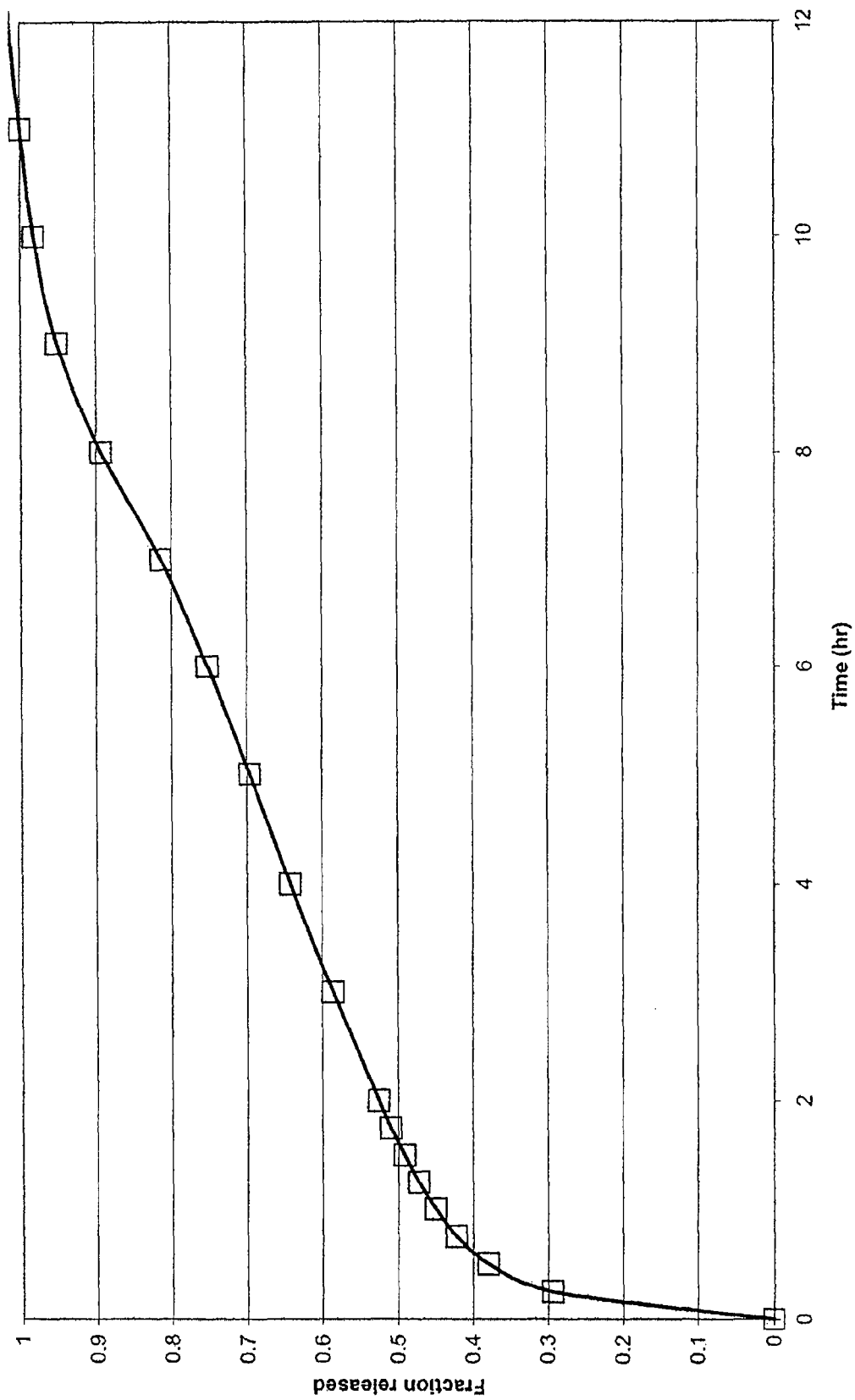
FIG. 3: In-vitro dissolution of Example 3

As shown in FIG. 3, the results of this Example demonstrate an in vitro release profile comprising a burst effect providing release of 20% of ibuprofen within 2 hours, followed by the sustained release of the remaining material evidencing release of 100% of the ibuprofen present in about 11 hours and greater than 90% in approximately 8 hours.

Example 4

In another embodiment, the formulation comprised ibuprofen, hydroxypropyl methylcellulose (HPMC K100M and HPMC K100LV), sodium carbonate, flow agents and tableting aids, in which HPMC K100M was present at a concentration of 17% by weight of ibuprofen, HPMC K100LV was present at a concentration of 17% by weight of ibuprofen, and sodium carbonate was present at a concentration of 25% by weight of ibuprofen within a compressed monolithic tablet. The specific formulation is as follows:

| Ex. 4 | mg |
| --- | --- |
| Ibuprofen | 600 |
| HPMC K100M | 100 |
| HPMC K100LV | 100 |
| MCC PH102 | 100 |
| $Na_2CO_3$, anhydrous | 150 |
| Silica, Syloid 244 | 20 |
| Mg Stearate | 10 |
| Total: | 1080 |

The formulation components were mixed in a V-blender. The resulting powder was compressed into tablets using conventional technologies. In this Example a combination of a medium to high viscosity HPMC and a low viscosity HPMC was used.

Figure 4:
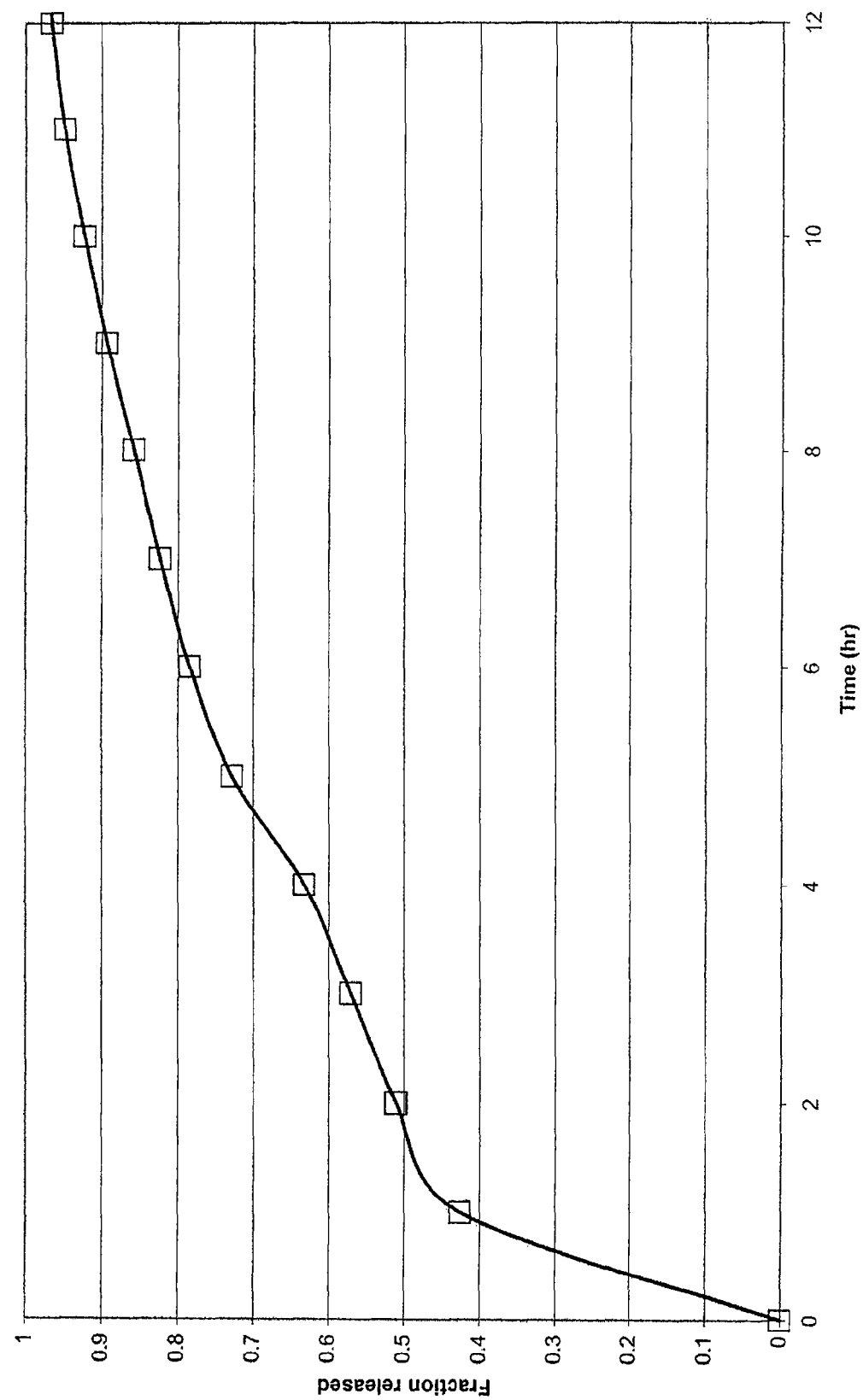
FIG. 4: In-vitro dissolution of Example 4

As shown in FIG. 4, the results of this Example demonstrate an in vitro release profile comprising a burst effect, followed by the sustained release of the remaining material. 20% of ibuprofen was released within 2 hours, followed by gradual sustained release, resulting in approximately 95% release after 12 hours.

Example 5

In another embodiment, the formulation comprised ibuprofen, hydroxypropyl methylcellulose (HPMC K100M), polyethylene oxide (PEO WSRN 301), sodium carbonate, glycine, flow agents and tableting aids, in which HPMC was present at a concentration of 17% by weight of ibuprofen, PEO was present at a concentration of 8.3% by weight of ibuprofen, glycine was present at a concentration of 3% by weight of ibuprofen and sodium carbonate was present at a concentration of 25% by weight of ibuprofen within a compressed monolithic tablet.

| Ex. 5 | mg |
| --- | --- |
| Ibuprofen | 600 |
| PEO 301 | 50 |
| HPMC K100M | 100 |
| MCC PH102 | 100 |
| $Na_2CO_3$, anhydrous | 150 |
| Glycine | 20 |
| Silica, Syloid 244 | 20 |
| Mg Stearate | 10 |
| Total: | 1050 |

The formulation components were mixed in a V-blender. The resulting powder was compressed into tablets using conventional compression technology.

Figure 5:
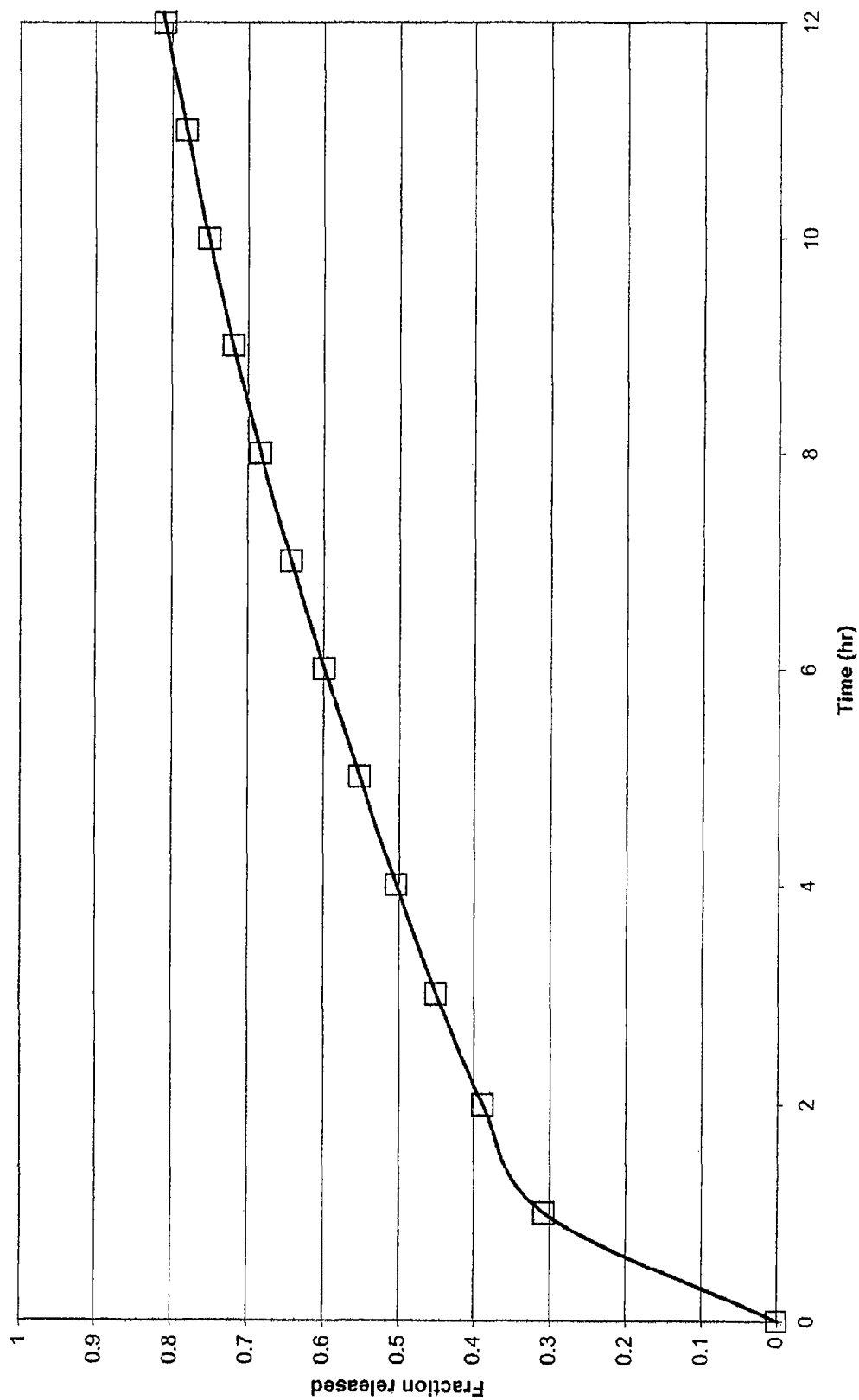
FIG. 5: In-vitro dissolution of Example 5

As shown in FIG. 5, the results of this Example demonstrate an in vitro release profile comprising a burst effect, followed by the sustained release of the remaining material. For this formulation 20% of ibuprofen was released within 2 hours, but incomplete release was evidenced after 12 hours.

Example 6

In another embodiment, the formulation comprised ibuprofen, hydroxypropyl methylcellulose (HPMC K15M), potassium carbonate, microcrystalline cellulose (PH105 and PH 200), flow agents and tableting aids, in which HPMC was present at a concentration of 32% by weight of ibuprofen, and potassium carbonate was present at a concentration of 17% by weight of ibuprofen within a compressed monolithic tablet.

| Ex. 6 | mg |
| --- | --- |
| Ibuprofen 90 grade | 600 |
| MCC PH 105 | 210 |
| HPMC K15M Prem | 190 |
| MCC PH 200 | 100 |
| $K_2CO_3$ anhydrous | 100 |
| | 1200 |

The formulation components were mixed in a V-blender. The resulting powder was compressed into tablets using conventional compression technology.

Figure 6:
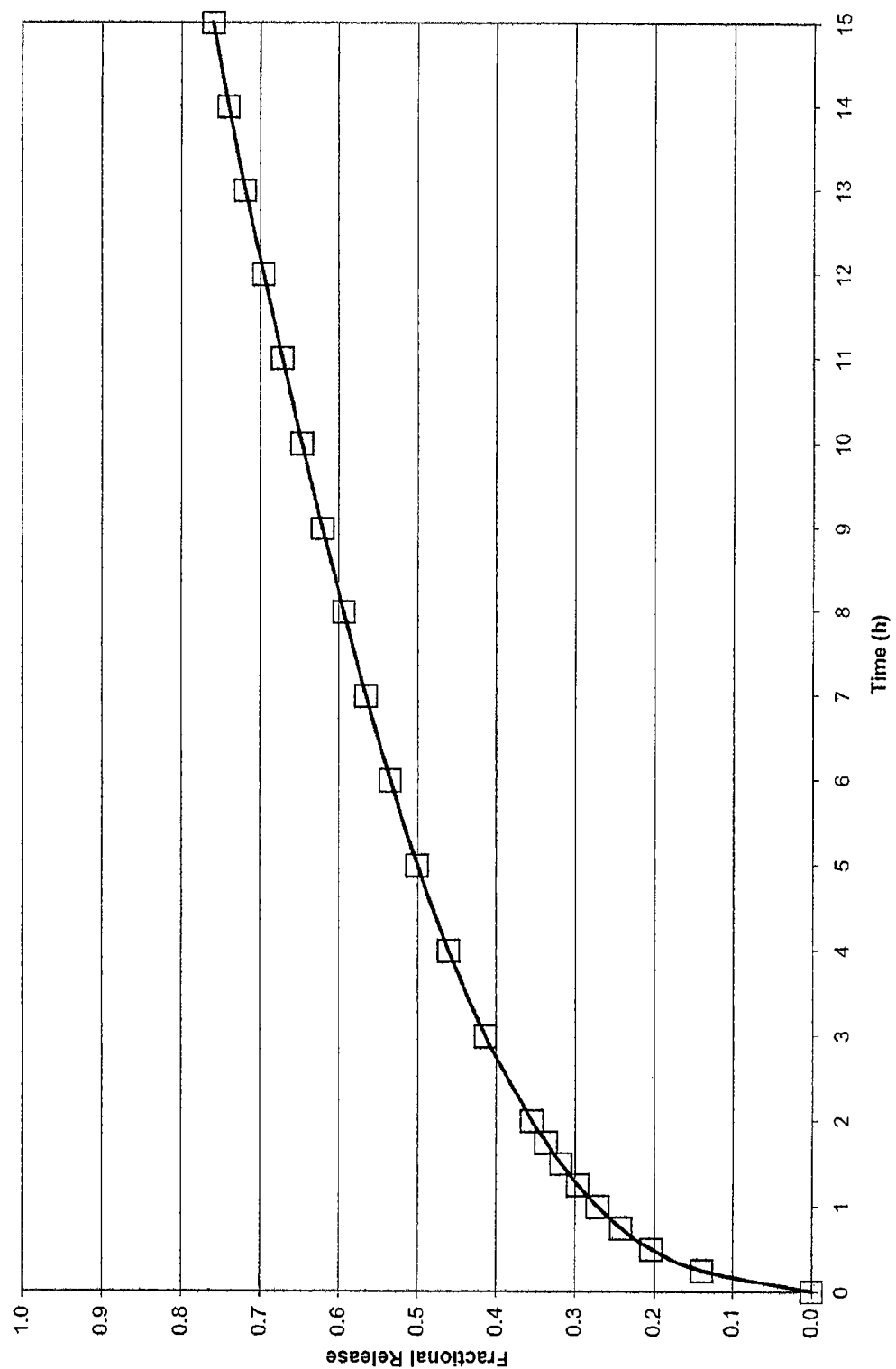
FIG. 6: In-vitro dissolution of Example 6

As shown in FIG. 6, the results of this Example demonstrate an in vitro release profile comprising a burst effect, followed by the sustained release of the remaining material. 20% of ibuprofen was released in under 2 hours, and release was thereafter sustained over a period of 15 hours. However, incomplete release was exhibited by the dosage form.

Example 7

In this embodiment, the formulation comprised ibuprofen, hydroxypropyl methylcellulose (HPMC K15M), sodium carbonate, microcrystalline cellulose (MCC PH105 and MCC PH200), in which HPMC was present at a concentration of 32% by weight of ibuprofen, sodium carbonate was present at a concentration of 17% by weight of ibuprofen, MCC PH105 was present at a concentration of 35%, and MCC PH200 was present at a concentration of 17% within a compressed monolithic tablet.

| Ex. 7 | Mg |
|---|---|
| Ibuprofen 90 grade | 600 |
| HPMC K15M Prem | 190 |
| MCC PH 105 | 210 |
| MCC PH 200 | 100 |
| Na$_2$CO$_3$ anhydrous | 100 |
| | 1200 |

All ingredients were passed through a 30-mesh screen. The ibuprofen and the MCC 105 were pre-blended in a V-blender. The resulting homogenous pre-blend was granulated with water, dried and subsequently blended with the remaining formulation components in a V-blender. The resulting powder was compressed into tablets using conventional compression technology.

Figure 7:
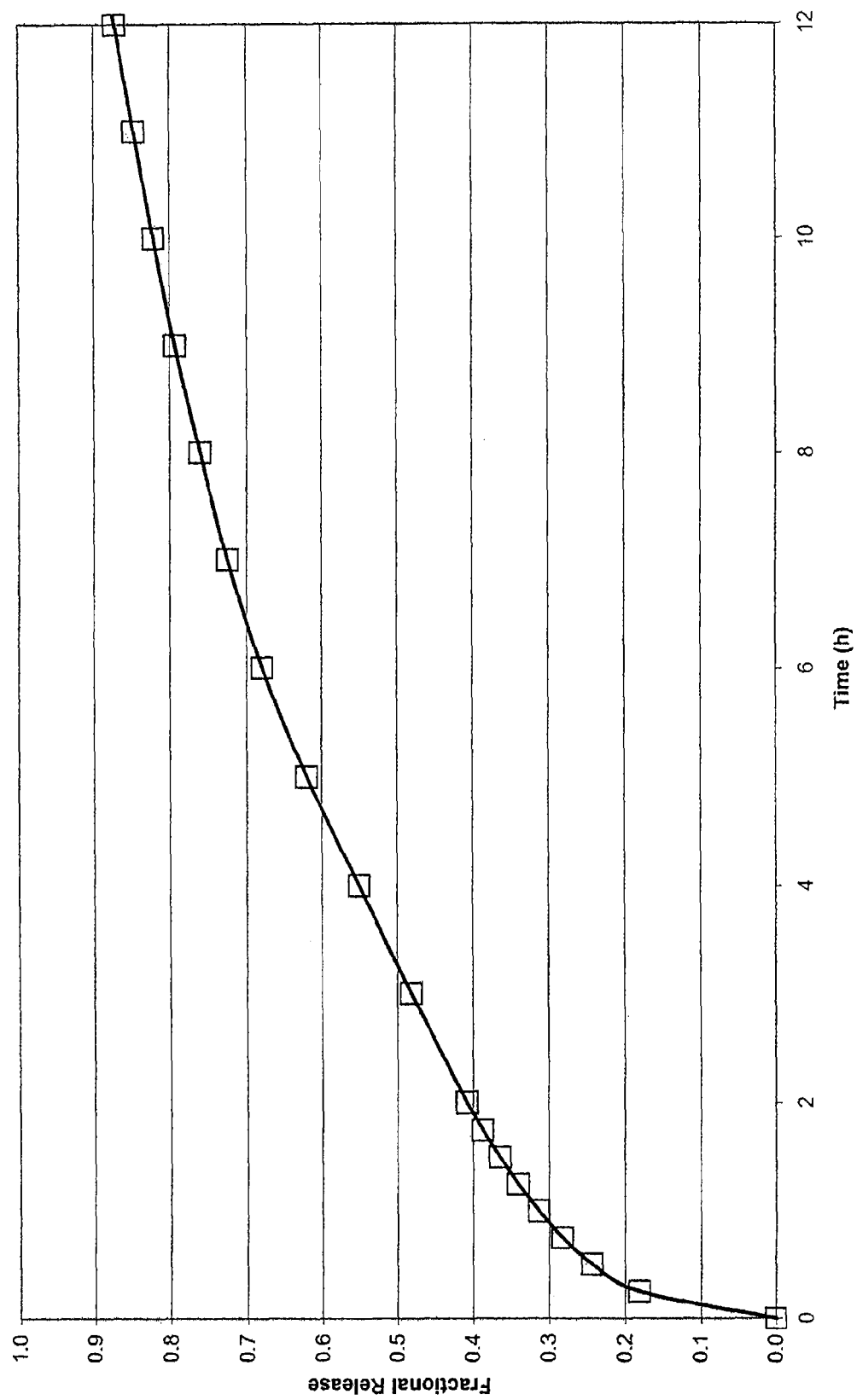
FIG. 7: In-vitro dissolution of Example 7

As shown in FIG. 7, this Example demonstrates an in vitro release profile comprising a burst effect, followed by the sustained release of the remaining material. The burst effect releases 20% of ibuprofen in under 2 hour, followed by relatively constant release over the next 10-12 hours and resulting in approximately 90% release after 12 hours.

Example 8

In the embodiment of Example 1a, the tablet resulting from the formulation was split into two equal parts, and both sections were placed into a dissolution vessel.

| Ex. 8 | mg |
|---|---|
| Ibuprofen 90 grade | 600 |
| HPMC K15M | 110 |
| HPMC K100LV | 100 |
| MCC PH102 | 100 |
| Na$_2$CO$_3$, anhydrous | 150 |
| Glycine | 15 |
| Silica, Syloid 244 | 20 |
| Mg Stearate | 10 |
| Total: | 1105 |

Figure 8:
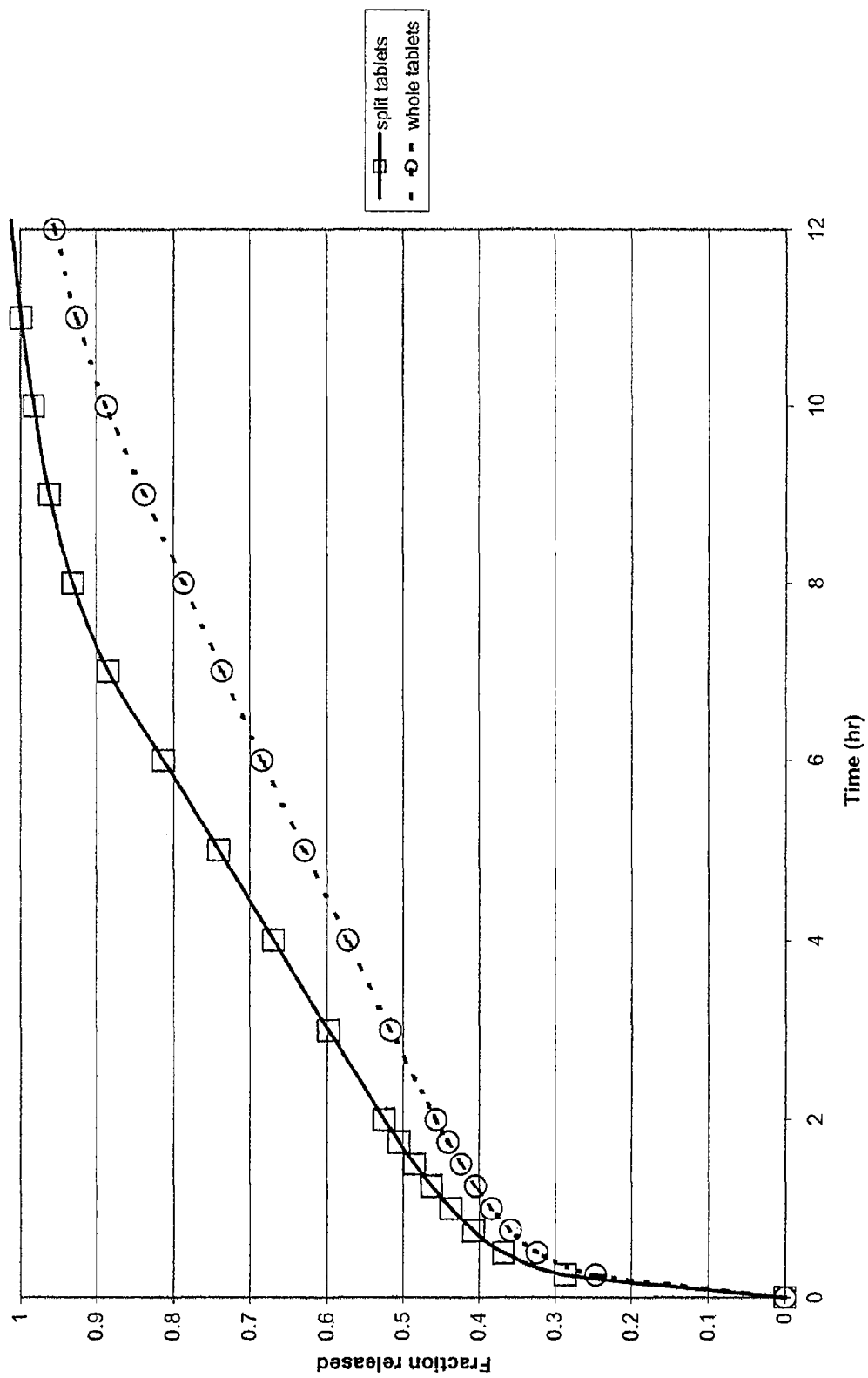
FIG. 8: In-vitro dissolution of Example 8

As shown in FIG. 8, the results of this Example demonstrates an in vitro release profile comprising a burst effect, followed by the sustained release of the remaining material, even when split into sections after tableting. In each case 20% of ibuprofen was released in less than one hour and substantially all the ibuprofen had been released at about 12 hours.

Example 9

In one embodiment, the formulation comprised ibuprofen, hydroxypropyl methylcellulose (HPMC K15M), sodium carbonate, microcrystalline cellulose (MCC PH 302), glycine and silica in which HPMC was present at a concentration of 33% by weight of ibuprofen, sodium carbonate was present at a concentration of 17% by weight of ibuprofen, and MCC PH 302 was present at a concentration of 33% within a compressed monolithic tablet. The specific formulation is as follows:

| Ex. 9 | mg |
|---|---|
| Ibuprofen 90 grade | 300 |
| HPMC K15M Prem | 100 |
| MCC PH 302 | 100 |
| Na$_2$CO$_3$ anhydrous | 50 |
| Glycine | 7.5 |
| Silica | 5.5 |
| Total: | 563 |

All ingredients were passed through a 30-mesh screen and blended in a V-blender. The resulting homogenous pre-blend was granulated with water, dried and subsequently blended with the remaining formulation components in a V-blender. The resulting powder was compressed into tablets using conventional technologies.

Figure 9:
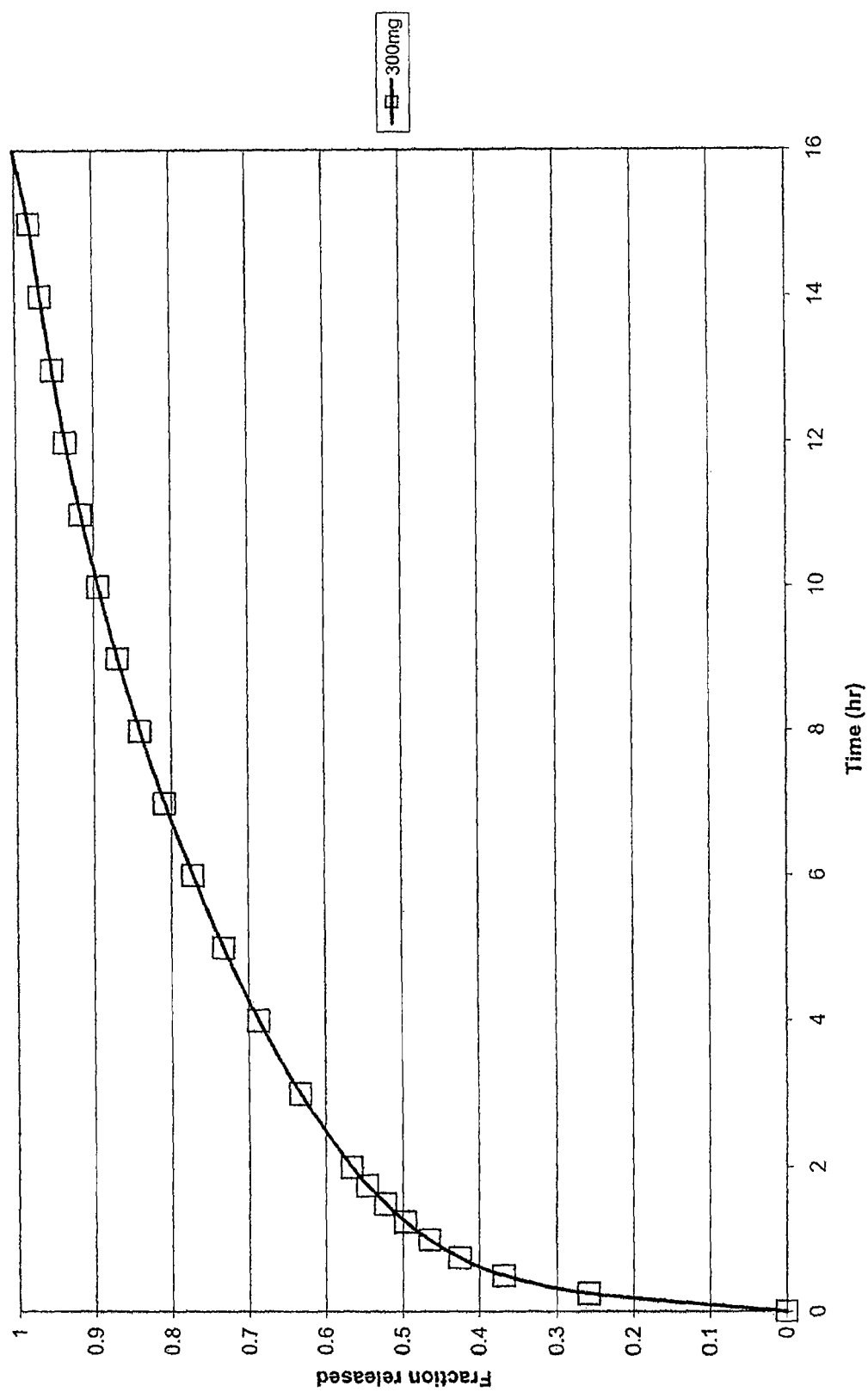
FIG. 9: In-vitro dissolution of Example 9

As shown in FIG. 9, the results of this Example demonstrate an in vitro release profile comprising a burst effect, followed by the sustained release of the remaining material. 20% of ibuprofen was released within 2 hours, about 90% release was obtained in about 9 hours followed by 100% release in under 16 hours.

Example 10

In another embodiment, the formulation comprised ibuprofen, hydroxypropyl methylcellulose (HPMC K4M), arginine, flow agents and tableting aids, in which HPMC K4M was present at a concentration of 32% by weight of ibuprofen, and arginine was present at a concentration of 17% by weight of ibuprofen within a compressed monolithic tablet.

| Ex. 10 | mg |
|---|---|
| Ibuprofen 90 grade | 600 |
| Silica | 5.5 |
| MCC PH 105 | 210 |
| HPMC K4M Prem | 190 |
| Arginine | 100 |
| Silica | 5.5 |
| Total: | 1111 |

The microcrystalline cellulose, MCC PH 105, and 5.5 mg of silica were pre-blended in a V-blender with ibuprofen. The remaining excipients were then blended with the dry pre-blended powder. The resulting tableting formulation was compressed into tablets using conventional technologies.

Figure 10:
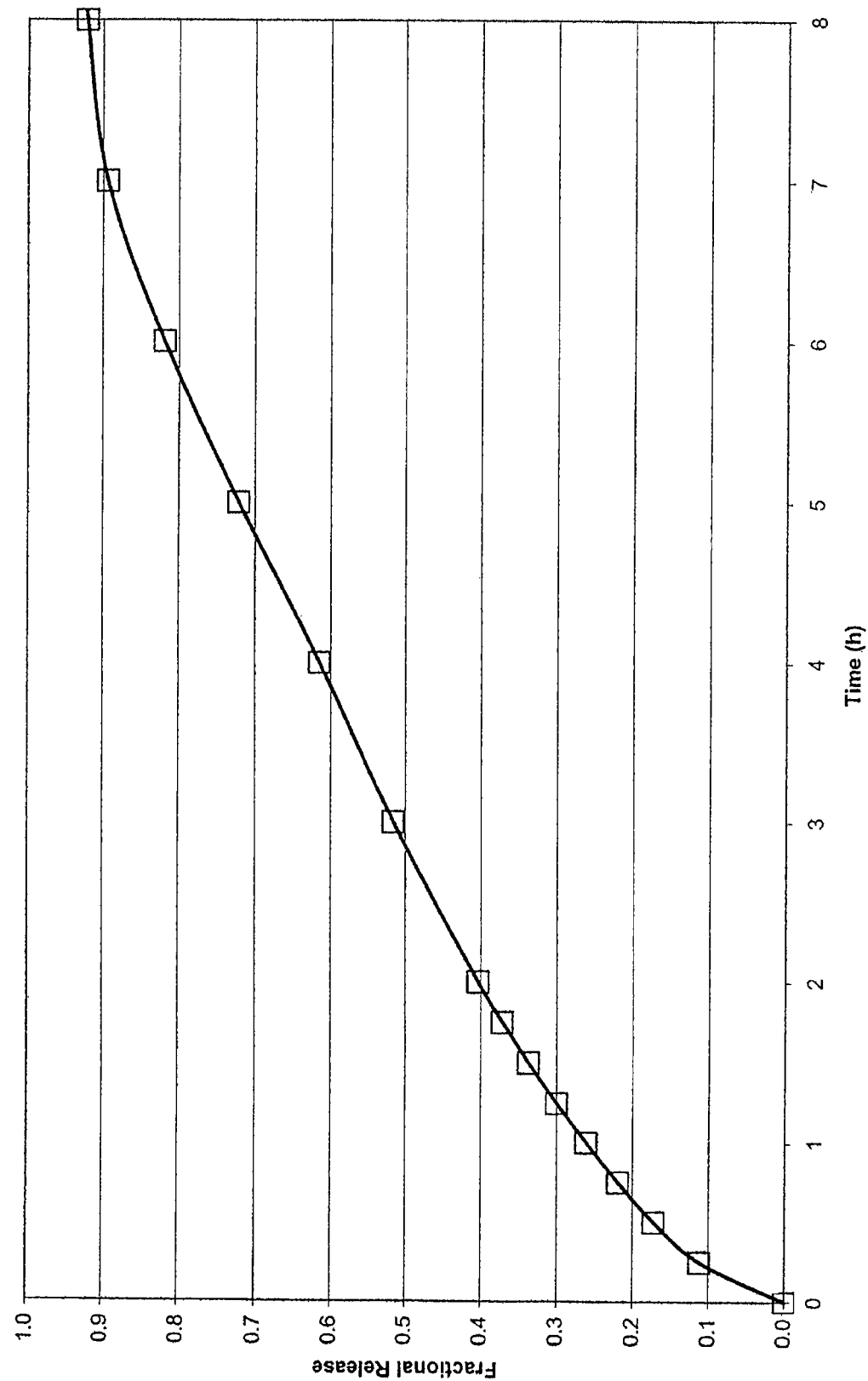
FIG. 10: In-vitro dissolution of Example 10

As shown in FIG. 10, the results of this Example demonstrate an in vitro release profile comprising a slight burst effect, followed by the sustained release of the remaining material. While the burst effect in this formulation produces somewhat delayed achievement of the percentage released, this formulation demonstrates in excess of 90% release over a period of 8 hours.

Example 11

In another embodiment, the formulation comprised ibuprofen, hydroxypropyl methylcellulose (HPMC K4M), sodium carbonate, arginine, flow agents and tableting aids, in which HPMC K4M was present at a concentration of 32% by weight of ibuprofen, sodium carbonate was present at concentration of 17% by weight of the ibuprofen, and arginine was present at a concentration of 17% by weight of ibuprofen within a compressed monolithic tablet.

| Ex. 11 | mg |
|---|---|
| Ibuprofen 90 grade | 600 |
| Silica | 5.5 |
| MCC PH 105 | 210 |
| HPMC K4M Prem | 190 |
| $Na_2CO_3$ anhydrous | 100 |
| MCC PH 200 | 100 |
| Arginine | 100 |
| Silica | 5.5 |
| Stearic Acid | 12 |
| Total: | 1323 |

The microcrystalline cellulose PH 105 and 5.5 mg of silica were pre-blended in a V-blender with ibuprofen to form a pre-blended powder. The remaining excipients were blended with the resulting pre-blended powder. The resulting tableting formulation was compressed into tablets using conventional technologies.

Figure 11:
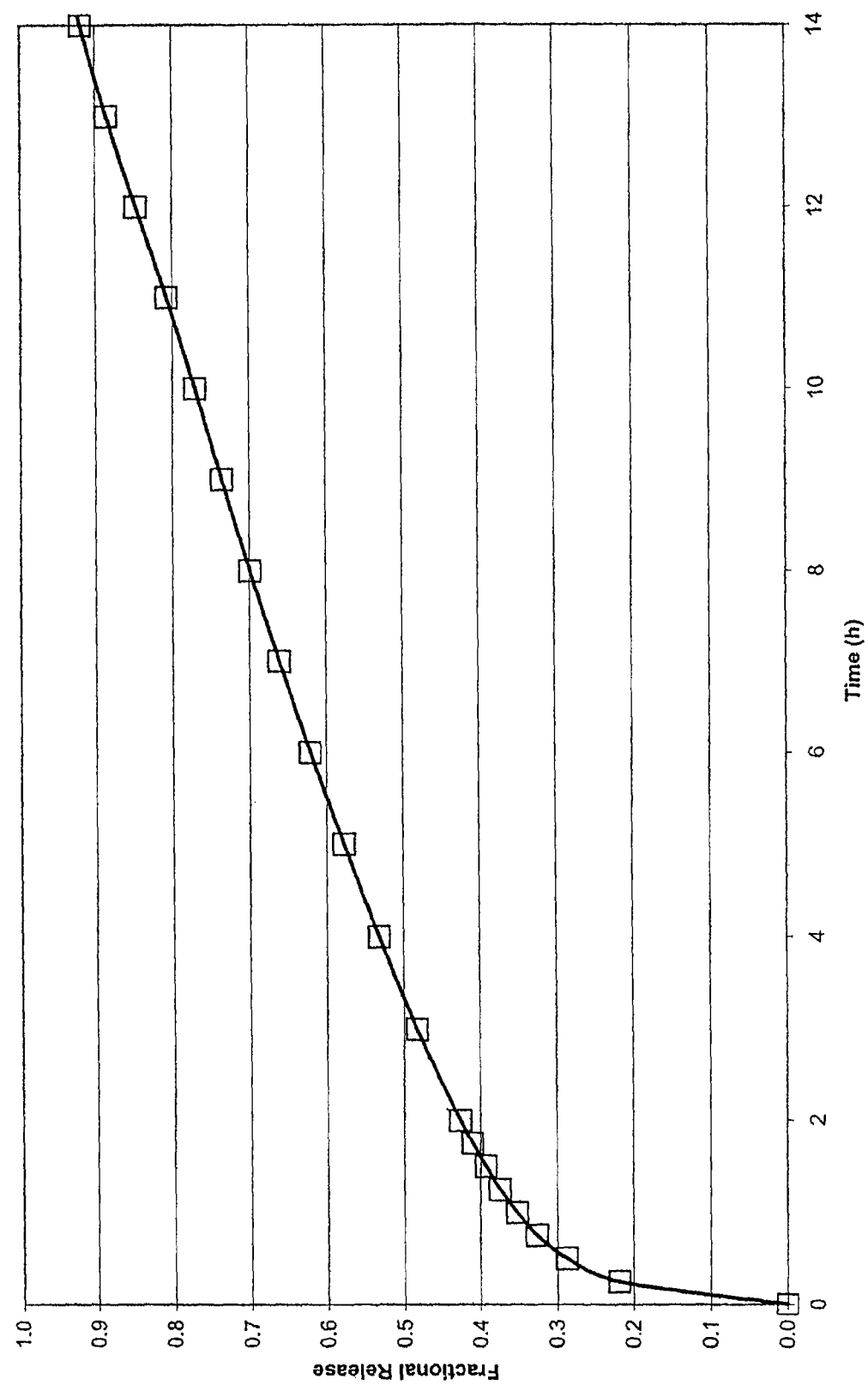
FIG. 11: In-vitro dissolution of Example 11

As shown in FIG. 11, the results of this Example demonstrate the in vitro release profile comprising a burst effect, followed by the sustained release of the remaining material. The initial release is greater than 20% of ibuprofen in less than two hours, and approximately 90% release over a period of 14 hours.

Example 12

In another embodiment, the formulation comprised ibuprofen, hydroxypropyl methylcellulose (HPMC K4M), microcrystalline cellulose (MCC 105), sodium carbonate, flow agents and various tableting aids, in which HPMC K4M was present at a concentration of 32% by weight of ibuprofen, sodium carbonate was present at concentration of 17% by weight of the ibuprofen, and tableting aid, either Lactopress (12a), dicalcium phosphate (12b), or pregelatinized starch (12c), was present at a concentration of 17% by weight of ibuprofen within a monolithic tablet.

| Ex. 12a | mg |
|---|---|
| Ibuprofen 90 grade | 600 |
| Silica | 5.5 |
| MCC PH 105 | 210 |
| HPMC K4M Prem | 190 |
| $Na_2CO_3$ anhydrous | 100 |
| Lactopress | 100 |
| Silica | 5.5 |
| Stearic acid | 12 |
| Total: | 1223 |

| Ex. 12b | mg |
|---|---|
| Ibuprofen 90 grade | 600 |
| Silica | 5.5 |
| MCC PH 105 | 210 |
| HPMC K4M Prem | 190 |
| $Na_2CO_3$ anhydrous | 100 |
| Dicalcium phosphate | 100 |
| Silica | 5.5 |
| Stearic acid | 12 |
| Total: | 1223 |

| Ex. 12c | mg |
|---|---|
| Ibuprofen 90 grade | 600 |
| Silica | 5.5 |
| MCC PH 105 | 210 |
| HPMC K4M Prem | 190 |
| $Na_2CO_3$ anhydrous | 100 |
| Starch 1500 | 100 |
| Silica | 5.5 |
| Stearic acid | 12 |
| Total: | 1223 |

All ingredients were passed through a 30-mesh screen. The ibuprofen, 5.5 mg of silica and the MCC 105 were pre-blended in a V-blender. The resulting homogenous pre-blend was granulated with water, dried, and subsequently blended with the remaining formulation components in a V-blender. The resulting tableting formulation was compressed into tablets using conventional technologies.

Figure 12:
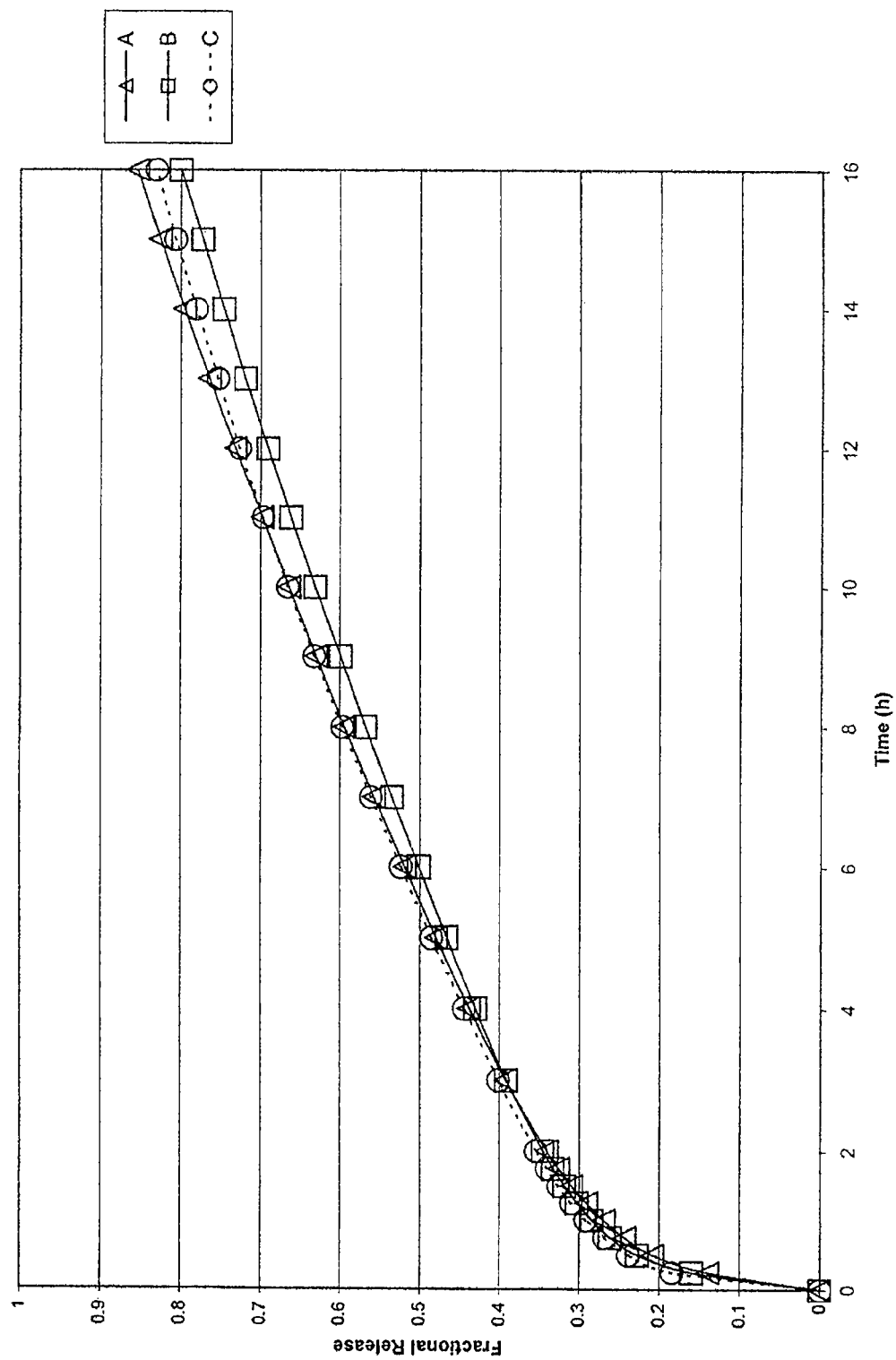
FIG. 12: In-vitro dissolution of Example 12

As shown in FIG. 12, the results of this Example demonstrate the invention is capable of an in vitro release profile comprising a burst effect, followed by the sustained release of the remaining material, with little or no alteration in release profile when the tableting aid selection is varied. The in vitro profile shows greater than 20% release before 2.0 hours with a constant rate release and at least 70% release by 14 hours.

Example 13

In another embodiment, the formulation comprised ibuprofen, hydroxypropyl methylcellulose (HPMC K4M), microcrystalline cellulose (MCC 105), sodium carbonate, flow agents and various tableting aids, in which HPMC K4M was present at a concentration of 32% by weight of ibuprofen, sodium carbonate was present at concentration of 17% by weight of the ibuprofen, and croscarmellose sodium was present at a concentration of 3% by weight of ibuprofen within a monolithic tablet.

| Ex. 13 | Mg |
|---|---|
| Ibuprofen 90 grade | 600 |
| Silica | 5.5 |
| MCC PH 105 | 210 |
| HPMC K4M Prem | 190 |
| $Na_2CO_3$ anhydrous | 100 |
| MCC PH 200 | 100 |
| Croscarmellose sodium | 18 |
| Silica | 5.5 |
| Stearic acid ~1% | 12 |
| Total: | 1241 |

All ingredients were passed through a 30-mesh screen. The ibuprofen, 5.5 mg of silica and the MCC 105 were blended in a V-blender for an extended period of time. The resulting homogenous pre-blend was granulated with water, dried and subsequently blended with the remaining formulation components in a V-blender. The resulting tableting formulation was compressed into tablets using conventional technologies.

Figure 13:
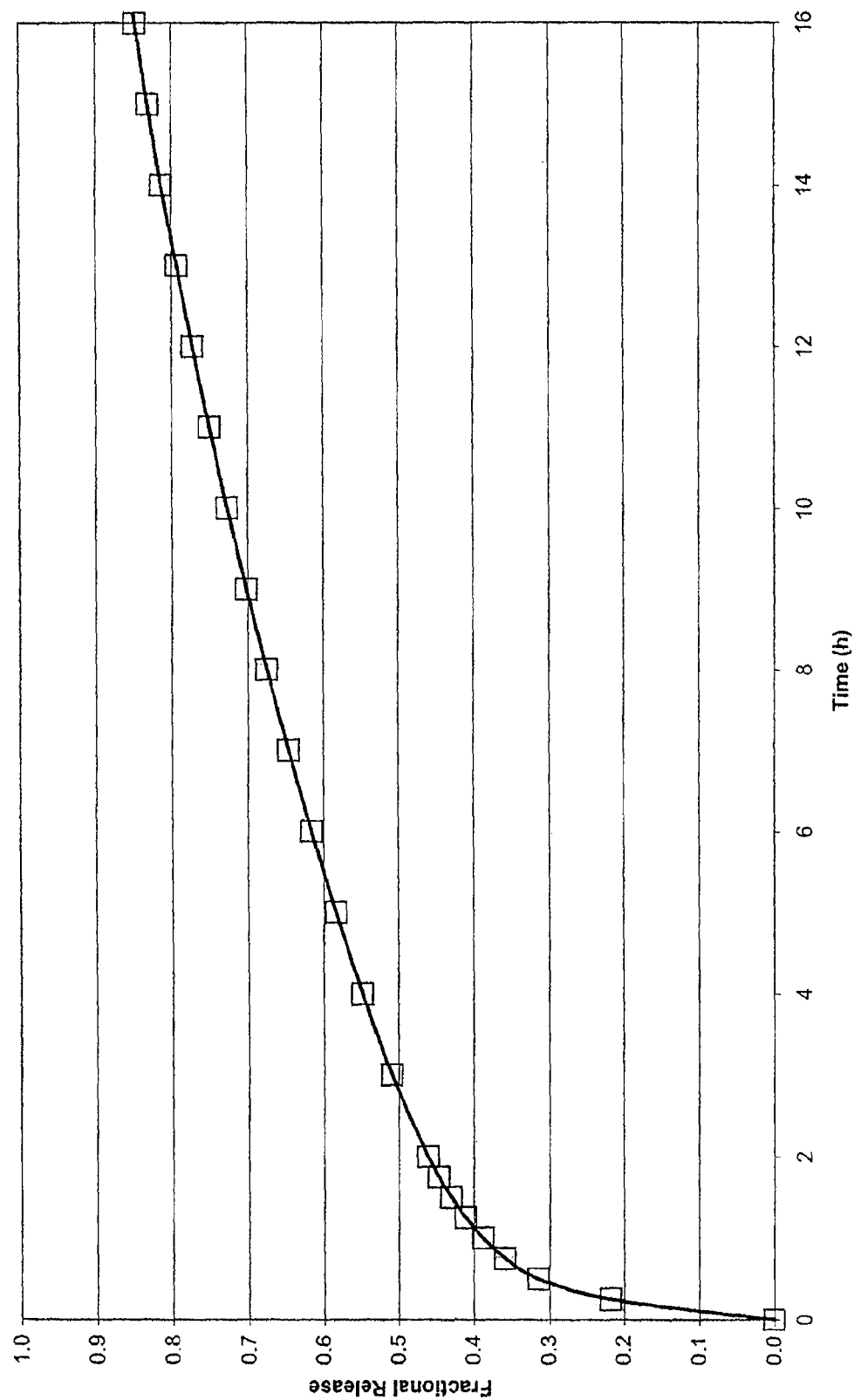
FIG. 13: In-vitro dissolution of Example 13

As shown in FIG. 13, the results of this Example demonstrates an in vitro release profile comprising a burst effect, followed by the sustained release of the remaining material. The in vitro profile shows greater than 20% release before 2.0 hours followed by a relatively constant rate release and at least 80% release by 14 hours.

Example 14

In another embodiment, the formulation comprised ibuprofen, hydroxypropyl methylcellulose (HPMC K4M), microcrystalline cellulose (MCC PH 105 and PH 200), glycine, croscarmellose sodium, flow agents and various tableting aids, in which HPMC K4M was present at a concentration of 32% by weight of ibuprofen, glycine was present at a concentration of 8% by weight of ibuprofen and croscarmellose sodium was present at a concentration of 6% by weight of ibuprofen within a monolithic tablet.

| Ex. 14 | Mg |
| --- | --- |
| Ibuprofen 90 grade | 600 |
| MCC PH 105 | 200 |
| Silica | 5.5 |
| HPMC K4M Prem | 190 |
| MCC PH 200 | 100 |
| Glycine | 50 |
| Croscarmellose sodium | 35 |
| Silica | 5.5 |
| Stearic acid ~1% | 12 |
| Total: | 1198 |

All ingredients were passed through a 30-mesh screen. The ibuprofen, 5.5 mg of silica and the MCC 105 were blended in a V-blender. The resulting homogenous pre-blend was granulated with water, dried and subsequently blended with the remaining formulation components in a V-blender. The resulting tableting formulation was compressed into tablets using conventional technologies.

Figure 14:
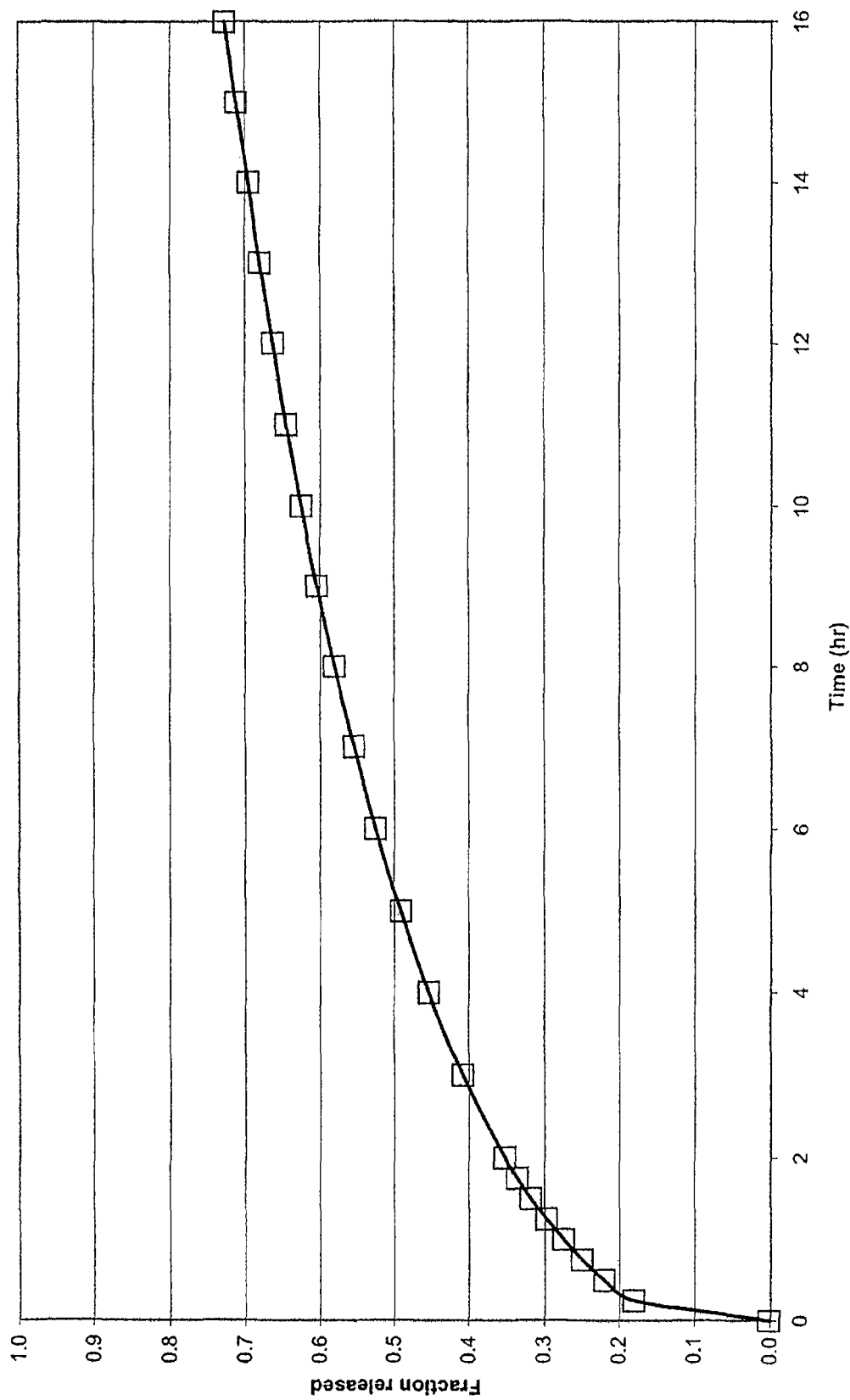
FIG. 14: In-vitro dissolution of Example 14

As shown in FIG. 14, the results of this Example demonstrate the invention is capable of an in vitro release profile comprising a burst effect, followed by the sustained release of the remaining material. The in vitro profile shows greater than 20% release before 2.0 hours with a constant rate release and at least 70% release by 14 hours.

Example 15

In another embodiment, the formulation comprised ibuprofen, polyethylene oxide (PEO 301 and PEO 60K), glycine, sodium carbonate, flow agents and various tableting aids, in which PEO was present at a concentration of 31% by weight of ibuprofen, sodium carbonate was present at concentration of 25% by weight of the ibuprofen, and glycine was present at a concentration of 38% by weight of ibuprofen within a monolithic tablet.

| Ex. 15 | Mg |
| --- | --- |
| Ibuprofen | 400 |
| PEO 301 | 50 |
| PEO 60K | 75 |
| Na2CO3 | 100 |
| Glycine | 150 |
| Maltodextrin M-580 | 100 |
| Stearic acid | 10 |
| Silica | 10 |
| Total: | 895 |

All ingredients were passed through a 30-mesh screen. The ibuprofen was blended with the formulation components in a V-blender. The resulting powder was compressed into tablets using conventional technologies.

Figure 15:
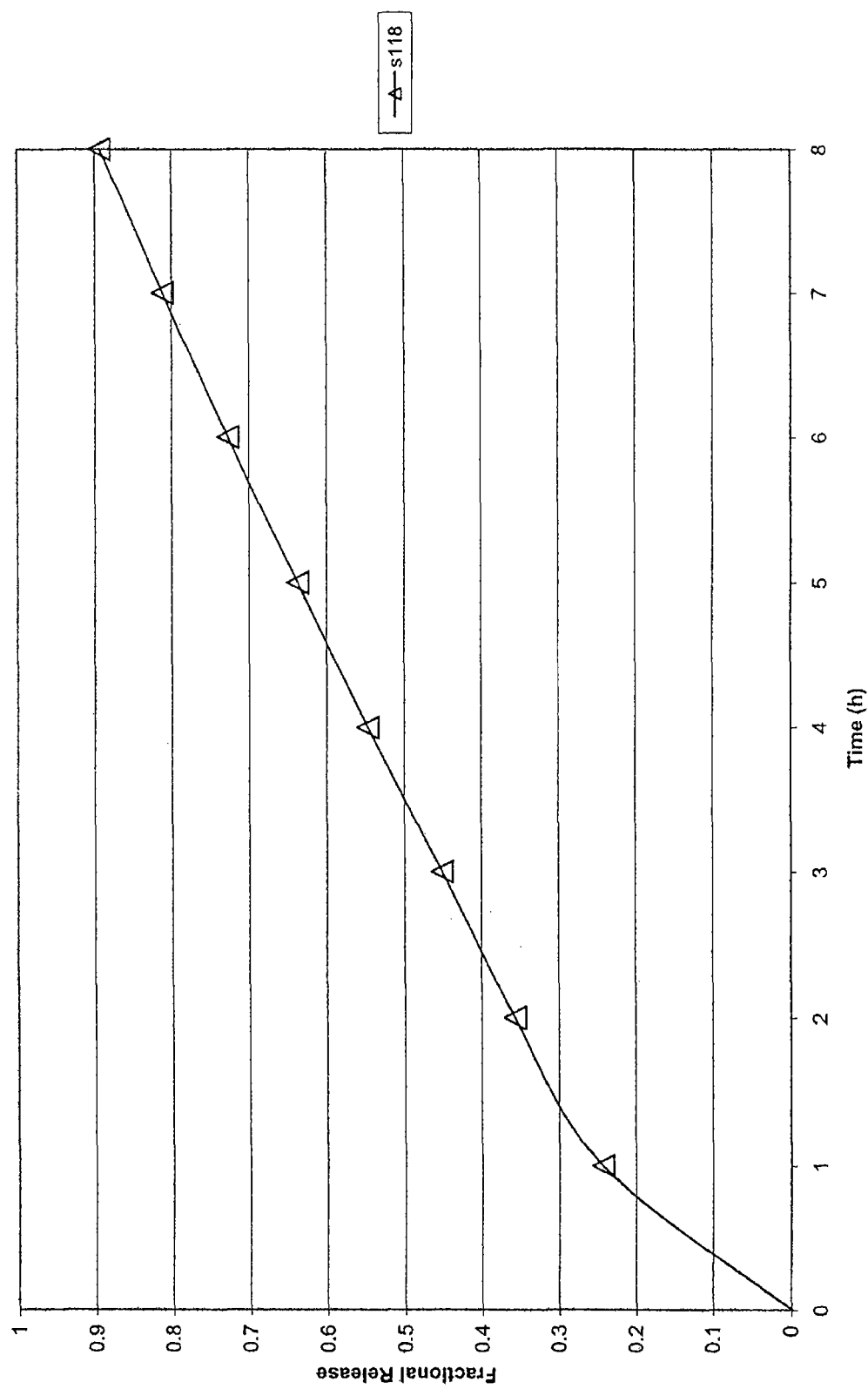
FIG. 15: In-vitro dissolution of Example 15

As shown in FIG. 15, the results of this Example demonstrate the invention is capable of an in vitro release profile comprising a burst effect, followed by the sustained release of the remaining material. The in vitro profile shows greater than 20% release before 2.0 hours with a constant rate release and at least 80% release by 8 hours.

Example 16

In another embodiment, the formulation comprised ibuprofen, polyethylene oxide (PEO 301, PEO 60K), glycine, sodium carbonate, flow agents and various tableting aids, in which PEO was present at a concentration of 25% by weight of ibuprofen, sodium carbonate was present at concentration of 25% by weight of the ibuprofen, and glycine was present at a concentration of 25% by weight of ibuprofen within a monolithic tablet.

| Ex. 16 | Mg |
| --- | --- |
| Ibuprofen | 400 |
| PEO 301 | 50 |
| PEO 60K | 50 |
| Na2CO3 | 100 |
| Glycine | 100 |
| Maltodextrin M-580 | 100 |
| Stearic acid | 10 |
| Silica | 10 |
| Total: | 820 |

All ingredients were passed through a 30-mesh screen. The ibuprofen was blended with the formulation components in a V-blender. The resulting powder was compressed into tablets using conventional technologies.

Figure 16:
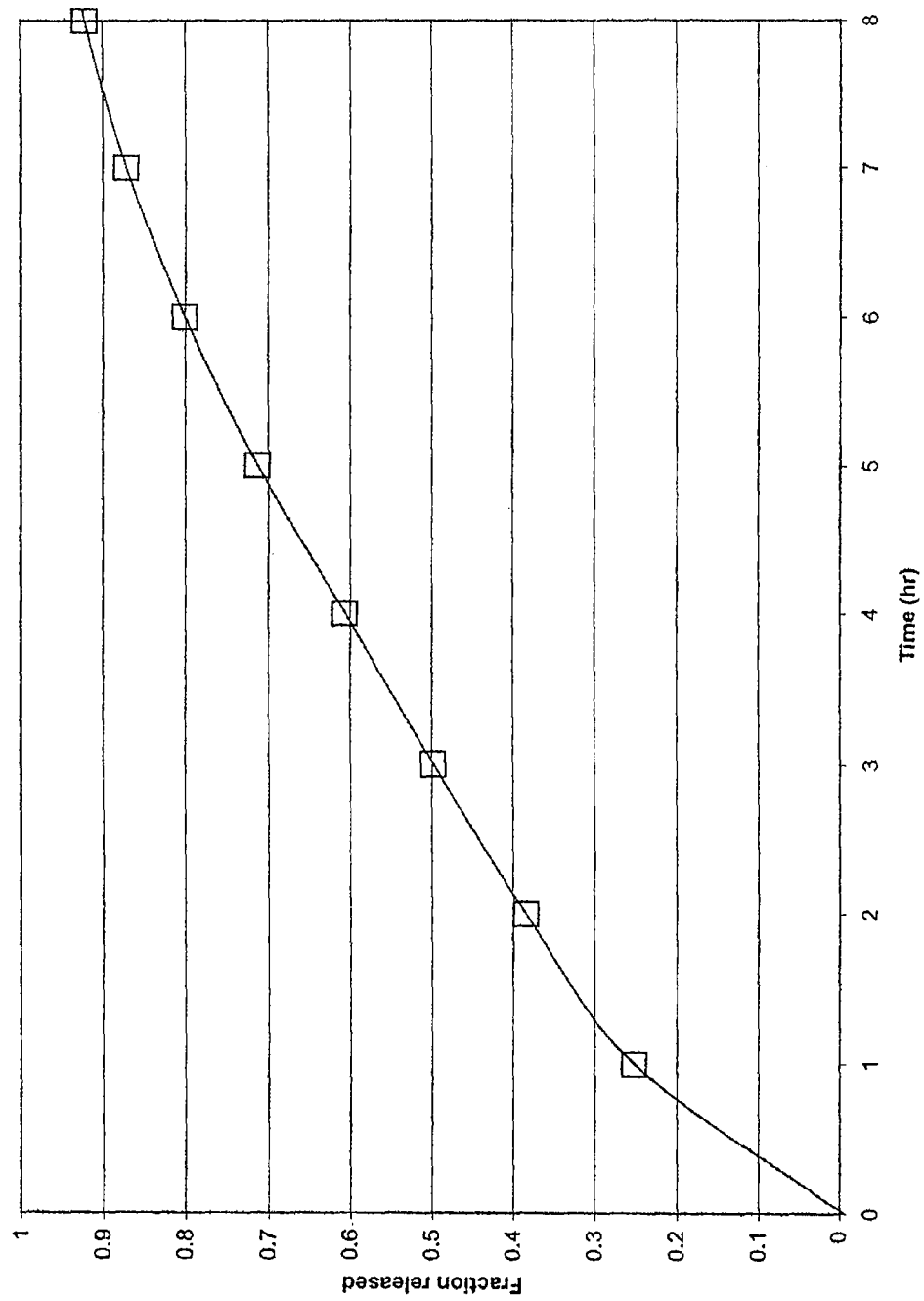
FIG. 16: In-vitro dissolution of Example 16

As shown in FIG. 16, the results of this Example demonstrate the invention is capable of an in vitro release profile comprising a burst effect, followed by the sustained release of the remaining material. The in vitro profile shows greater than 20% release before 2.0 hours with a constant rate release and at least 90% release by 8 hours.

Example 17

In another embodiment, the formulation comprised ibuprofen, polyethylene oxide (PEO 301), glycine, sodium carbonate, and a stearic acid lubricant, in which PEO was present at a concentration of 25% by weight of ibuprofen, sodium carbonate was present at concentration of 25% by weight of the ibuprofen, and glycine was present at a concentration of 25% by weight of ibuprofen within a monolithic tablet.

| Ex. 17 | Mg |
|---|---|
| Ibuprofen | 400 |
| PEO 301 | 100 |
| Na2CO3 | 100 |
| Glycine | 100 |
| Stearic acid | 10 |
| Total: | 710 |

All ingredients were passed through a 30-mesh screen. The ibuprofen was blended with the formulation components in a V-blender. The resulting powder was compressed into tablets using conventional technologies.

The results of this Example demonstrate the invention is capable of an in vitro release profile comprising a burst effect, followed by the sustained release of the remaining material. The in vitro profile shows greater than 20% release before 2.0 hours with a constant rate release and at least 80% release.

Example 18

In another embodiment, the formulation comprised ibuprofen, polyethylene oxide (PEO 301), glycine, sodium carbonate, croscarmellose sodium, flow agents and various tableting aids, in which PEO was present at a concentration of 25% by weight of ibuprofen, sodium carbonate was present at concentration of 25% by weight of the ibuprofen, and glycine was present at a concentration of 25% by weight of ibuprofen within a monolithic tablet. The specific formulation was as follows:

| Ex. 18 | Mg |
|---|---|
| Ibuprofen | 400 |
| PEO 301 | 100 |
| Na2CO3 | 100 |
| Glycine | 100 |
| Croscarmellose Sodium | 50 |
| DCP | 150 |
| Stearic acid | 10 |
| Total: | 910 |

All ingredients were passed through a 30-mesh screen. The ibuprofen was blended with the formulation components in a V-blender. The resulting powder was compressed into tablets using conventional technologies.

The results of this Example demonstrate the invention is capable of an in vitro release profile comprising a burst effect, followed by the sustained release of the remaining material. The in vitro profile shows greater than 20% release before 2.0 hours with a constant rate release and at least 90% release.

Comparative In Vitro Data

BRUFEN RETARD is a commercially available in Europe as a sustained release formulation of ibuprofen. BRUFEN RETARD tablets are specially formulated to allow the gradual release of active substance giving stable levels and a prolonged duration of effect over the dosage interval. BRUFEN RETARD is a film coated tablet with 800 mg of ibuprofen. BRUFEN RETARD is indicated for its analgesic and anti-inflammatory effect in the treatment of rheumatoid arthritis (including juvenile rheumatoid arthritis or Still's disease), ankylosing spondylitis, and osteo-arthritis. BRUFEN RETARD is indicated in the treatment of non-articular rheumatism including fibrositis. BRUFEN RETARD is indicated in periarticular conditions such as frozen shoulder (capsulitis), bursitis, tendinitis, tenosynovitis and low-back pain. BRUFEN RETARD can also be used in soft-tissue injuries such as sprains and strains. BRUFEN RETARD is also indicated for its analgesic effect in the relief of mild to moderate pain such as dysmenorrhoea, dental, post-episiotomy pain and post-partum pain.

Example 19

Figure 17:
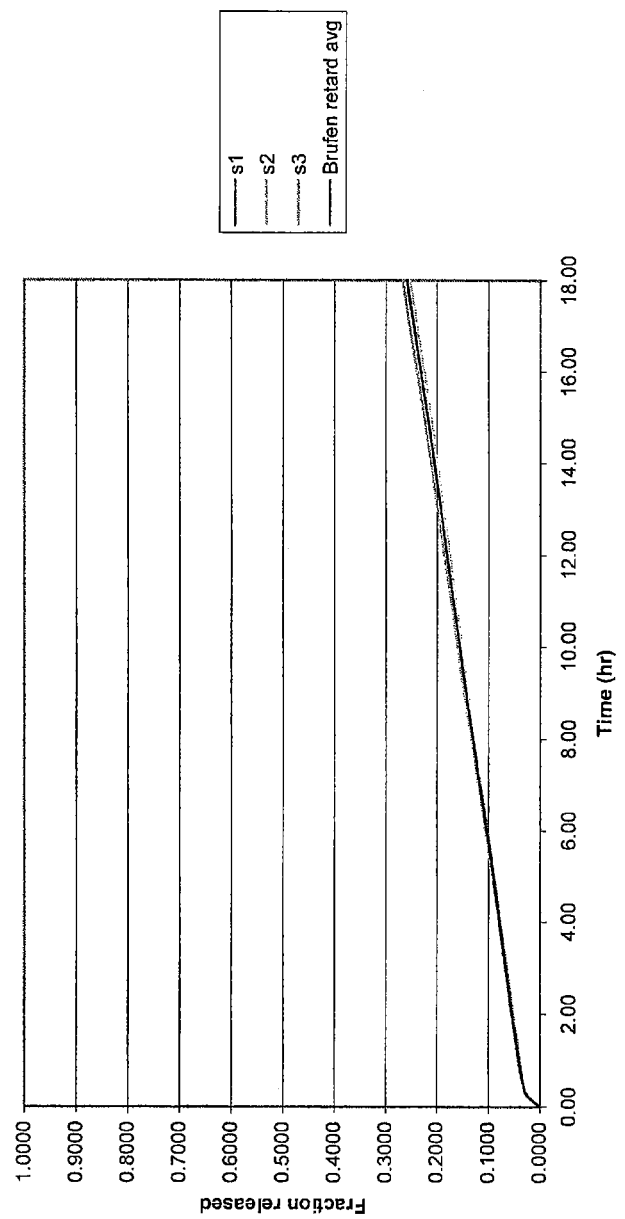
FIG. 17: In-vitro dissolution of BRUFEN RETARD, an extended release form of Ibuprofen available for sale in Europe.

BRUFEN RETARD tablet in vitro release performance was evaluated in a type II dissolution apparatus in 900 mL $KH_2PO_4$ buffer, pH 7.2, at 50 rpm paddle speed. As shown in FIG. 17, the results of this Example demonstrate the in vitro data results of BRUFEN RETARD. The figure shows that BRUFEN RETARD is incapable of an in vitro release profile comprising a burst effect, followed by the sustained release of the remaining material. BRUFEN RETARD fails to deliver to release at least 20% of ibuprofen by 2.0 hours with a constant rate of release with at least 70% release at 14 hours.

Example 20

In Vivo Trial

In the in vivo testing, serum concentrations of subjects taking tablets comprising the modified release formulation of the present invention were compared with serum concentrations of subjects taking immediate release ibuprofen tablets (Motrin® IB 200 mg and Motrin® 600 mg). Tablets comprising the modified release formulation of the present invention demonstrated a burst effect followed by sustained release and therapeutic concentration at extended time periods that the other two immediate release formulations did not. The minimum mean serum plasma ibuprofen concentration in the blood of the subject was between 8 and 10 µg/ml for Motrin® IB.

The in vivo behavior of modified release solid dosages of 1a and 1b from Example 1 were compared to the in vivo behavior of an immediate release formulation (MOTRIN®). The open-label study involved 10 healthy male volunteers over the age of 18. Following an overnight fast of at least ten hours, each subject received either one 600 mg dose of one of the two above described modified release tablets or 200 mg every four hours for 3 doses of the immediate release formulation of MOTRIN® IB or one 600 mg tablet of MOTRIN®. 88 blood samples were taken prior to dosing and at specific intervals up to 12 hours after dosing.

The blood samples were kept in ice bath prior to centrifugation and were centrifuge as soon as possible under refrigerated condition at 35000 rpm for seven minutes. The collected plasma from each blood collection tube was aliquotted into pre-cooled labeled polypropylene tubes. The samples were kept in an ice bath, then stored frozen at minus 25° C.±10° C. until assayed.

Figure 18:
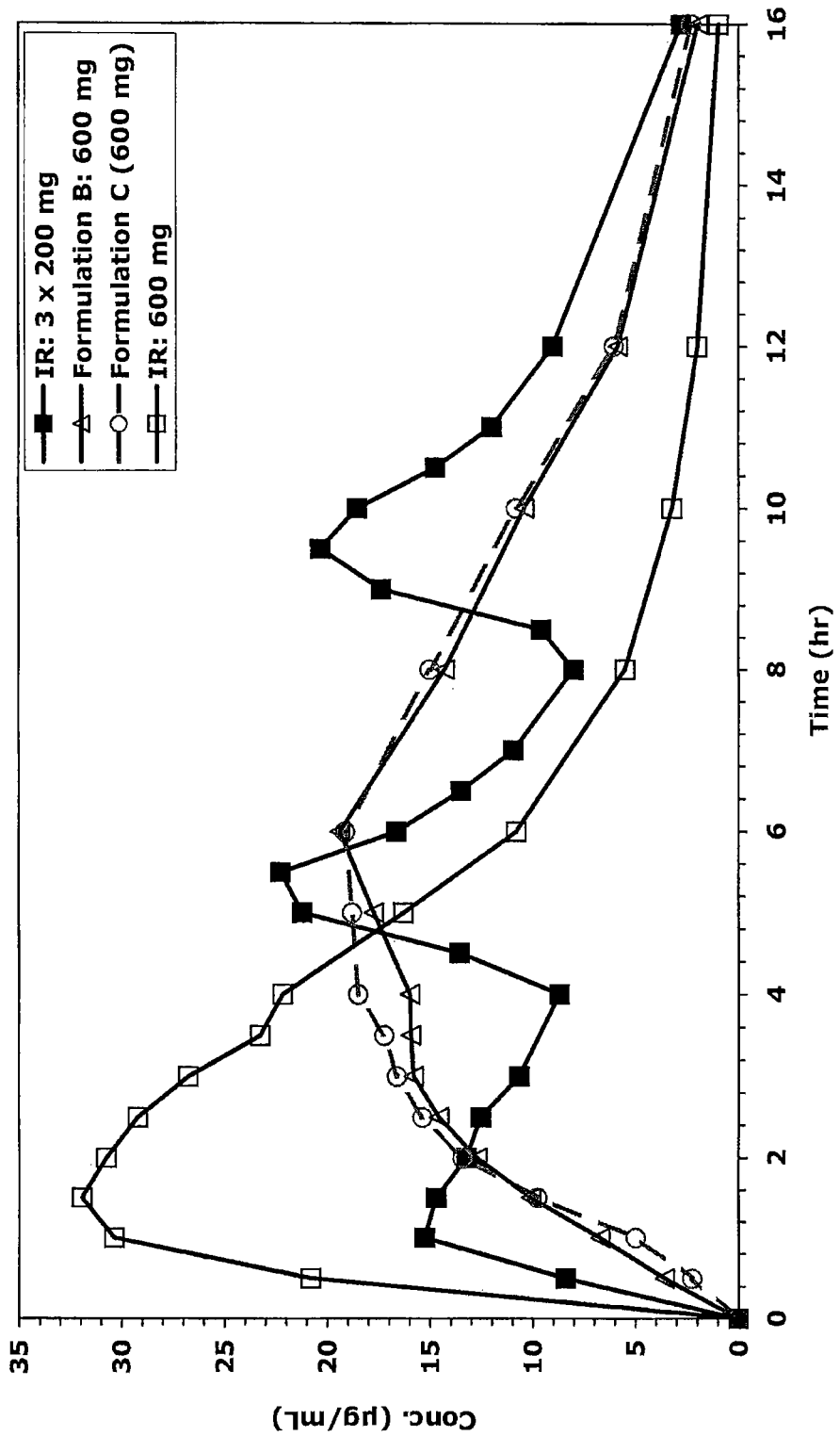
FIG. 18: In-vivo data from comparison of present invention versus Motrin®

The plasma samples were analyzed by a fully validated HPLC method. The analytes were separated by reverse phase chromatography. Evaluation of the assay was carried out by the construction of an eight point calibration curve (excluding zero concentration) covering the range of 0.400 µg/ml to 51.200 µg/ml (in human plasma) for ibuprofen. The slope and intercept of the calibration curves were determined through weighted linear regression analysis ($1/conc.^2$). The results are depicted in FIG. 18.

TABLE 1

| | Summary of 90% CI | | | | | |
|---|---|---|---|---|---|---|
| | Reference: D (1 × 600 mg) | | | Reference: E (3 × 200 mg) | | |
| Formulation | $C_{max}$ | $AUC_{0-last}$ | $AUC0_{-\infty}$ | $C_{max}$ | $AUC_{0-last}$ | $AUC_{0-\infty}$ |
| B (1a) | 42.4-53.8 | 96.2-115 | 97.0-116 | 67.0-85.0 | 86.9-104 | 86.3-103 |
| C (1b) | 44.7-57.0 | 96.9-116 | 98.7-119 | 70.7-90.3 | 87.5-105 | 87.7-106 |
| D | — | — | — | 140-179 | 82.3-99.2 | 80.9-97.7 |
| E | 55.9-71.5 | 101-122 | 102-124 | — | — | — |

D is a 3 × 200 mg MOTRIN ® IB
E is a 1 × 600 mg MOTRIN ®

Treatments (B & C) Versus Treatment E

The systematic exposure to ibuprofen after the administration of the one 600 mg ibuprofen tablet 1a or 1b (Treatments B & C) was similar to that obtained when compared to the administration of one MOTRIN® 600 mg tablet. The peak exposure to ibuprofen from one 600 mg ibuprofen tablet 1a or 1b (Treatments A-C) was significantly lower than that from the MOTRIN® 600 mg tablet. The absorption time was modified comparing one 600 mg ibuprofen tablet 1a or 1b (Treatments B & C) with median $T_{max}$ value of 5.0 h to a 1.5 h $T_{max}$ of one MOTRIN® 600 mg tablet.

Treatments (B & C) Versus Treatment D

The systematic exposure to ibuprofen after the administration of the one 600 mg ibuprofen tablet 1a or 1b (Treatments B & C) was similar to that obtained when compared to the administration of three MOTRIN® IB 200 mg tablets. The peak exposure to ibuprofen from one 600 mg ibuprofen tablet 1a or 1b (Treatments B & C) was significantly lower than that from three MOTRIN® IB 200 mg tablets. The absorption time was modified comparing one 600 mg ibuprofen tablet 1a or 1b (Treatments B & C) with median $T_{max}$ value of 5.0 h to a 1.0 h $T_{max}$ of three MOTRIN® IB 200 mg tablet.

FIG. 18 depicts the results discussed above. Treatment D shows an initial burst that falls to a valley at four hours and the second tablet is administered. This valley again happens at the eighth hour. This valley constitutes the minimum plasma concentration for ibuprofen to be considered therapeutic. A mean ibuprofen plasma concentration of about 6.4-10 µg/ml is considered the concentration of ibuprofen needed in the blood to be considered clinically effective. Treatment E shows an extreme initial burst of ibuprofen followed by a steady decline that falls below therapeutic threshold at about 6 hours.

Treatments B and C have an initial burst of ibuprofen that reaches the level of 6.4 µg/ml at about 0.5 to 1 hour and maintains the level until about hour 12. The present invention provides for a single dosage of ibuprofen that provides an initial burst similar to an immediate release formulation of ibuprofen and then provides a mean ibuprofen plasma concentration of above 6.4 µg/ml for about 12 hours.

Example 21

In another embodiment, the formulation comprised two viscosities of HPMC, two particle sizes of silicified MCC, in combination with croscarmellose and glycine, and a stearic acid lubricant, in which the combined HPMC was present at about 32% based on the ibuprofen present in the formulation in HPMC K100LV and HPMC K4M were present in a weight ratio of about 2:1 respectively, and silicified MCC was present as Prosolv50 and Prosolv90 in a weight ratio of about 2:1 at a combined concentration of about 50% based on the ibuprofen present in the formulation within a monolithic tablet.

| Ex. 21 | mg/tablet |
|---|---|
| HPMC K4M | 125 |
| HPMV K100LV | 65 |
| MCC (Prosolv SMCC 50, approx 60 um) | 200 |
| MCC (Prosolv SMCC 90, approx 110 um) | 100 |
| Croscarmellose Sodium (AcDiSol) | 35 |
| Glycine | 50 |
| Ibuprofen, (90 grade) | 600 |
| Silicon Dioxide | 12 |
| Stearic Acid | 12 |
| Total | 1199 |

All ingredients were passed through a 30-mesh screen. The ibuprofen was pre-blended with the 6 mg silica at about a 1:100 ratio in a V-blender. The resulting pre-blended ibuprofen powder was blended with the remaining excipients. The resulting powder was compressed into tablets using conventional technologies. The results of this Example, shown in FIG. 19, demonstrate the invention is capable of an in vitro release profile comprising a burst effect, followed by the sustained release of the remaining material over a period of 16 hours, with greater than 30% release occurring within 2.0 hours.

Example 22

In another embodiment, the formulation comprised two viscosities of HPMC, two particle sizes of silicified MCC, in combination with croscarmellose and glycine, and a stearic acid lubricant. This formulation is similar in its proportions to the formulation of example 21, except that the resulting monolithic tablets contained approximately half of the quantities of example 21. Thus this formulation comprised a two-tablet dosage unit having essentially the same ingredients as example 21.

| Ex. 22 | mg/tablet |
|---|---|
| HPMC K4M | 63 |
| HPMV K100LV | 33 |
| MCC (Prosolv SMCC 50, approx 60 um) | 100 |
| MCC (Prosolv SMCC 90, approx 110 um) | 50 |
| Croscarmellose Sodium (AcDiSol) | 18 |
| Glycine | 25 |
| Ibuprofen, (90 grade) | 300 |
| Silicon Dioxide | 6 |
| Stearic Acid | 6 |
| Total | 600 |

All ingredients were passed through a 30-mesh screen. The ibuprofen was pre-blended with the 3 mg silica in a V-blender at about a 1:100 ratio. The dry pre-blended powder was blended with the remaining excipients. The resulting powder was compressed into tablets using conventional technologies. The results of this Example demonstrate the invention is capable of an in vitro release profile comprising a burst effect, followed by the sustained release of the remaining material.

Example 23

This formulation comprised two different viscosities of HPMC and two different particle sizes of silicified MCC, together with croscarmellose and glycine, as also exemplified in Example 21. In this formulation the silicified MCC was present at a concentration of about 42% based on the ibuprofen present, and the weight ratio of Prosolv 50 to Prosolve 90 was about 1:1.5.

| Ex. 23 | mg/tablet |
| --- | --- |
| HPMC K4M | 125 |
| HPMV K100LV | 65 |
| MCC (Prosolv SMCC 50, approx 60 um) | 100 |
| MCC (Prosolv SMCC 90, approx 110 um) | 150 |
| Croscarmellose Sodium (AcDiSol) | 35 |
| Glycine | 50 |
| Ibuprofen, (90 grade) | 600 |
| Silicon Dioxide | 12 |
| Stearic Acid | 12 |
| Total | 1049 |

All ingredients were passed through a 30-mesh screen. The ibuprofen was pre-blended with 6 mg silica in a V-blender at about a 1:100 ratio. The dry pre-blended ibuprofen powder was then blended with the remaining excipients. The resulting powder was compressed into tablets using conventional technologies.

The results of this Example demonstrate the invention is capable of an in vitro release profile comprising a burst effect, followed by the sustained release of the remaining material.

What is claimed is:

1. A modified release formulation of ibuprofen providing immediate and sustained drug release, comprising:
   a hydrophilic polymer;
   300 to 800 mg of ibuprofen in solid dosage form uniformly dispersed in said polymer; a dissolution additive dispersed in said hydrophilic polymer in an amount in the range of 10% to 35% by weight of the ibuprofen, said dissolution additive comprising an alkali metal salt, an amino acid having a neutral to alkaline side chain, croscarmellose sodium, or a combination thereof;
   and an inert formulation additive dispersed in said hydrophilic polymer in an amount in the range of 15% to 75% by weight of the ibuprofen,
   wherein said hydrophilic polymer comprises a first hydroxypropyl methylcellulose (HPMC) having a viscosity of about 100 cps and a second HPMC having a viscosity between about 200 cps to about 50,000 cps,
   wherein said formulation is in a solid dosage form comprising a monolithic tablet and releases at least 20% of the ibuprofen within 2 hours following oral administration or exposure to an agitated aqueous medium of a single dosage unit, then thereafter releases ibuprofen at a relatively constant rate in a substantially linear relationship between percentage of ibuprofen released and elapsed time over a period of at least 8 hours, and wherein at least 70% of the ibuprofen is released over a period of not more than 14 hours following such administration or exposure.

2. The formulation of claim 1, wherein ibuprofen is present in each tablet in an amount of about 300 mg, 400 mg, or 600 mg.

3. The formulation of claim 1, wherein ibuprofen is present in each tablet in an amount of about 600 mg.

4. The formulation of claim 1, wherein each hydroxypropyl methylcellulose is present at a concentration of 17% to 42% by weight of the ibuprofen.

5. The formulation of claim 1, wherein the viscosity of the second HPMC is about 4,000 cps.

6. The formulation of claim 1, wherein the first HPMC is present at a concentration in the range of 5% to 20% by weight of the ibuprofen and the second HPMC has a viscosity of about/1000 cps and is present at a concentration in the range of about 10% to about 30% by weight of the ibuprofen.

7. The formulation of claim 1, wherein said second HPMC has a viscosity selected from the group consisting of 200 cps, 1,000 cps, 2,000 cps, 4,000 cps, 10,000cps, 15,000 cps, and 50,000 cps.

8. The formulation of claim 1, wherein the inert formulation additive comprises a first inert formulation additive having a first average particle size and a second inert formulation additive having a second average particle size, wherein the first and second inert formulation additives are each present in an amount in the range of 15% to 35% by weight of the ibuprofen.

9. The formulation of claim 8, wherein said first inert formulation additive comprises a first microcrystalline cellulose having the first average particle size and said second inert formulation additive comprises a second microcrystalline cellulose having the second average particle size, wherein each such microcrystalline cellulose is present at a concentration in the range of about 15% to about 35% by weight of the ibuprofen, the combination of which comprises from about 40% to about 60% by weight of the ibuprofen.

10. The formulation of claim 9, wherein the first average particle size is about 60 icrons and the second average particle size is about 110 microns.

11. The formulation of claim 1, wherein the inert formulation additive comprises microcrystalline cellulose.

12. The formulation of claim 11, wherein the inert formulation additive further comprises silica, stearic acid, magnesium stearate, lactose, pre-gelatinized starch, dicalcium phosphate, or a combination of any of them.

13. The formulation of claim 1, wherein: the inert formulation additive comprises a first microcrystalline cellulose having a first average particle size and a second microcrystalline cellulose having a second average particle size; and the dissolution additive comprises glycine as the amino acid having a neutral to alkaline side chain, and croscarmellose sodium.

14. The formulation of claim 13, wherein the first and second microcrystalline cellulose comprise silicified microcrystalline cellulose.

15. A modified release formulation of ibuprofen providing immediate and sustained drug release, comprising:
   a hydrophilic polymer;
   300 to 800mg of ibuprofen in solid dosage form uniformly dispersed in said polymer; dissolution additives dispersed in said hydrophilic polymer in an amount in the range of 10% to 35% by weight of the ibuprofen, said dissolution additives comprising glycine and croscarmellose sodium;

and inert formulation additives dispersed in said hydrophilic polymer in an amount in the range of 15% to 75% by weight of the ibuprofen, wherein said inert formulation additives comprise silica, stearic acid, a first silicified microcrystalline cellulose having an average particle size of about 60 microns, and a second silicified microcrystalline cellulose having an average particle size of about 110 microns, and wherein said first and second silicified microcrystalline celluloses are each present in an amount in the range of 15% to 35% by weight of the ibuprofen;

wherein said hydrophilic polymer comprises a first hydroxypropyl methylcellulose (HPMC) having a viscosity of about 100 cps and a second HPMC having a viscosity of about 4,000 cps, and wherein said formulation is in a solid dosage form comprising a monolithic tablet and releases at least 20% of the ibuprofen within 2 hours following oral administration or exposure to an agitated aqueous medium of a single dosage unit, then thereafter releases ibuprofen at a relatively constant rate in a substantially linear relationship between percentage of ibuprofen released and elapsed time over a period of at least 8 hours, and wherein at least 70% of the ibuprofen is released over a period of not more than 14 hours following such administration or exposure.

\* \* \* \* \*

UNITED STATES PATENT AND TRADEMARK OFFICE
CERTIFICATE OF CORRECTION

| | | |
|---|---|---|
| PATENT NO. | : 9,028,869 B2 | Page 1 of 1 |
| APPLICATION NO. | : 12/706429 | |
| DATED | : May 12, 2015 | |
| INVENTOR(S) | : Michael Hite et al. | |

It is certified that error appears in the above-identified patent and that said Letters Patent is hereby corrected as shown below:

In the Claims

COLUMN 20, LINES 16-17, in CLAIM 6, DELETE: "has a viscosity of about/1000 cps and"

Signed and Sealed this
Twenty-third Day of June, 2015

Michelle K. Lee
*Director of the United States Patent and Trademark Office*